(12) United States Patent
Tuckermann et al.

(10) Patent No.: US 8,906,858 B2
(45) Date of Patent: Dec. 9, 2014

(54) METHOD FOR THE PROPHYLACTIC OR THERAPEUTIC TREATMENT OF GLUCOCORTICOID-INDUCED OSTEOPOROSIS

(71) Applicant: Fritz-Lipmann-Institut E. V. Leibniz-Institut Fuer Altersforschung, Jena (DE)

(72) Inventors: Jan Tuckermann, Jena (DE); Alexander Rauch, Merzdorf (DE); Susanne Ostermay, Jena (DE); Ulrike Baschant, Erfurt (DE)

(73) Assignee: Fritz-Lipmann-Institut E. V. Leibniz-Institut fuer Altersforschung, Jena (DE)

( * ) Notice: Subject to any disclaimer, the term of this patent is extended or adjusted under 35 U.S.C. 154(b) by 0 days.

(21) Appl. No.: 13/707,823

(22) Filed: Dec. 7, 2012

(65) Prior Publication Data
US 2013/0171097 A1    Jul. 4, 2013

Related U.S. Application Data

(63) Continuation-in-part of application No. PCT/EP2011/059409, filed on Jun. 7, 2011.

(60) Provisional application No. 61/352,048, filed on Jun. 7, 2010.

(51) Int. Cl.
| | |
|---|---|
| A61K 38/20 | (2006.01) |
| A61K 31/00 | (2006.01) |
| A61K 31/222 | (2006.01) |
| A61K 45/06 | (2006.01) |
| C07C 219/28 | (2006.01) |
| A61K 31/216 | (2006.01) |
| A61K 31/57 | (2006.01) |

(52) U.S. Cl.
CPC .............. *A61K 38/204* (2013.01); *A61K 31/00* (2013.01); *A61K 31/222* (2013.01); *A61K 45/06* (2013.01); *C07C 219/28* (2013.01); *A61K 31/216* (2013.01); *A61K 31/57* (2013.01); *A61K 38/2073* (2013.01)
USPC .......... 514/16.9; 424/85.2; 514/171; 514/546

(58) Field of Classification Search
None
See application file for complete search history.

(56) References Cited

U.S. PATENT DOCUMENTS

| | | | |
|---|---|---|---|
| 2002/0039567 A1* | 4/2002 | Wallimann et al. ........... | 424/85.1 |
| 2003/0055030 A1 | 3/2003 | De Bosscher et al. | |
| 2009/0156672 A1 | 6/2009 | Budunova et al. | |

FOREIGN PATENT DOCUMENTS

WO   2007/071452 A1   6/2007

OTHER PUBLICATIONS

Maruta et al (Clin Exp Metastasis. 2009;26(2):133-41. Epub Oct. 25, 2008).*
Suda et al (Bone. Aug. 1995;17(2 Suppl):87S-91S).*
Richards et al (Cytokine. Jun. 2000;12(6):613-21).*
Bamberger et al (Mol Cell Endocrinol. Mar. 14, 1997;127(1):71-9).*
Vlasselaer et al (Prog Growth Factor Res. 1992;4(4):337-53).*
Cornish et al (Endocrinology. Mar. 1993;132(3):1359-66).*
Dore (Cleveland Clinic Journal of Medicine Aug. 2010 vol. 77(8); 529-536).*
Aline Bozec et al: "Osteoclast size is controlled by Fra-2 through LIF/LIF-receptor signalling and hypoxia", in: Nature, vol. 454, No. 7201, Jul. 10, 2008, pp. 221-225.
Valerie Gossye et al: "Differential mechanism of NF-kB inhibition by two glucocorticoid receptor modulators in rheumatoid arthritis synovial fibroblasts", in: Arthritis & Rheumatism, vol. 60, No. 11, Nov. 1, 2009, pp. 3241-3250.
Kido S et al: "Down-regulation of interleukin-11 may be involved in the pathogenesis of glucocorticoid-induced osteoporosi s.", in: Journal of Bone and Mineral Research, vol. 17, No. Suppl 1, Sep. 2009, p. S134 & Twenty-Fourth Annual Meeting of the American Society for Bone and Mineral Research; San Antonio, Texas, USA; Sep. 20-24, 2002.
A Dovio et al: "Autocrine down-regulation of glucocorticoid receptors by interleukin-11 in human osteoblast-like cell lines", in: Journal of Endocrinology, vol. 177, No. 1, Apr. 1, 2003), pp. 109-117.
K. De Bosscher et al: "A fully dissociated compound of plant origin for inflammatory gene repression", in: Proceedings of The National Academy of Sciences, vol. 102, No. 44, Nov. 1, 2005, pp. 15827-15832.
Ronacher K et al: "Ligand-selective transactivation and transrepression via the glucocorticoid receptor: Role of cofactor interaction", in: Molecular and Cellular Endocrinology, Elsevier Ireland LTD, IE, vol. 299, No. 2, Feb. 27, 2009, pp. 219-231.

(Continued)

*Primary Examiner* — Brian J Gangle
*Assistant Examiner* — Andrea McCollum
(74) *Attorney, Agent, or Firm* — Joyce von Natzmer; Agris & von Natzmer LLP

(57) ABSTRACT

The present invention relates to a method for the prophylactic and/or therapeutic treatment of glucocorticoid induced osteoporosis comprising maintaining or restoring AP-1 activity or AP-1-mediated effects, for example by LIF treatment. The method may additionally comprise a method for the treatment of a medical condition associated with inflammation comprising inhibition of NF-KB activity, for example by glucocorticoid (GC) treatment. The present invention therefore also relates to a method for the treatment and/or prevention of glucocorticoid induced osteoporosis comprising the administration of an effective amount of LIF to a subject, preferably in combination with GC treatment.

19 Claims, 27 Drawing Sheets

(56) References Cited

OTHER PUBLICATIONS

G. Van Loo et al: "Antiinflammatory Properties of a Plant-Derived Nonsteroidal, Dissociated Glucocorticoid Receptor Modulator in Experimental Autoimmune Encephalomyelitis", in: Molecular Endocrinology, vol. 24, No. 2, Feb. 1, 2010, pp. 310-322.

Alexander Rauch et al: "Glucocorticoids Suppress Bone Formation by Attenuating Osteoblast Differentiation via the Monomeric Glucocorticoid Receptor", in: Cell Metabolism, vol. 11, No. 6, Jun. 8, 2010, pp. 517-531.

S. Robertson et al: "Abrogation of Glucocorticoid Receptor Dimerization Correlates with Dissociated Glucocorticoid Behavior of Compound A", in: Journal of Biological Chemistry, vol. 285, No. 11, Mar. 12, 2010, pp. 8061-8075.

Peter Herrlich: "Cross-talk between glucocorticoid receptor and AP-1", in: Oncogene, vol. 20, No. 19, Apr. 30, 2001, pp. 2465-2475.

Ray et al: "Understanding Glucocorticoids", in: Horizons in Medicine 18: Updates on Major Clinical Advances, Jan. 1, 2007, pp. 167-168.

* cited by examiner

Southern Blot

PCR

|  | 10 weeks females | | 10 weeks males | |
|---|---|---|---|---|
|  | GR$^{flox}$ | GR$^{Runx2cre}$ | GR$^{flox}$ | GR$^{Runx2cre}$ |
| Rump-length (mm) | 64.35 ± 0.87 | 65.38 ± 1.09 | 67.62 ± 1.21 | 71.25 ± 0.09** |
| Tibial Length (mm) | 17.28 ± 0.13 | 17.21 ± 0.17 | 17.10 ± 0.35 | 17.43 ± 0.24 |
| Tibial width (mm) | 2.60 ± 0.16 | 2.84 ± 0.17 | 3.08 ± 0.14 | 3.00 ± 0.16 |
| L6 length (mm) | 3.29 ± 0.01 | 3.34 ± 0.01 | 3.18 ± 0.07 | 3.38 ± 0.17 |
| L6 width (mm) | 3.80 ± 0.25 | 3.85 ± 0.17 | 4.37 ± 0.16 | 4.70 ± 0.22* |

FIG. 16

|  | 10 weeks females | | 10 weeks males | |
|---|---|---|---|---|
|  | GR$^{wt}$ | GR$^{dim}$ | GR$^{wt}$ | GR$^{dim}$ |
| Rump-length (mm) | 64.03 ± 1.50 | 60.70 ± 1.30* | 65.03 ± 1.71 | 63.40 ± 2.66* |
| Tibial Length (mm) | 17.58 ± 0.26 | 16.93 ± 0.22** | 17.92 ± 0.30 | 17.70 ± 0.17 |
| Tibial width (mm) | 2.64 ± 0.17 | 2.60 ± 0.14 | 2.87 ± 0.43 | 2.56 ± 0.02 |
| L6 length (mm) | 3.29 ± 0.01 | 3.19 ± 0.01 | 3.18 ± 0.03 | 2.81 ± 0.03 |
| L6 width (mm) | 3.94 ± 0.33 | 3.75 ± 0.13 | 2.36 ± 0.03 | 1.90 ± 0.03 |

METHOD FOR THE PROPHYLACTIC OR THERAPEUTIC TREATMENT OF GLUCOCORTICOID-INDUCED OSTEOPOROSIS

FIELD OF THE INVENTION

The present invention relates to a method for the prophylactic or therapeutic treatment of glucocorticoid induced osteoporosis comprising inducing, maintaining or restoring activator protein 1 (AP-1) activity or AP-1-mediated effects, for example by Leukaemia inhibitory factor (LIF1) treatment. The method may additionally comprise a method for the treatment of a medical condition associated with inflammation comprising inhibition of nuclear factor 'kappa-light-chain-enhancer' of activated B-cells (NF-KB) activity, for example by glucocorticoid (GC) treatment. The present invention therefore also relates to a method for the treatment or prevention of glucocorticoid induced osteoporosis comprising the administration of An effective/therapeutically relevant amount of LIF to a subject, preferably in combination with GC treatment. The invention therefore relates to agents and/or methods that exhibit anti-inflammatory effects due to their NF-KB inhibitory effects but do not lead to GC-induced osteoporosis (GIO) due to either an absence of AP-1 inhibitory activity, or maintenance or restoration of AP-1 activity or one or more effects of AP-1 activity, such as by maintaining LIF expression or by direct treatment with LIF, in particular in cells of the osteoblastic lineage.

BACKGROUND OF AND INTRODUCTION TO THE INVENTION

Although glucocorticoids (GCs) are widely used to treat allergic and autoimmune diseases, their application is accompanied by severe side effects, including detrimental effects on the skeleton being one of the major complications (James et al., 2007). GC-induced reduction of bone mass by GCs is believed to involve systemic effects and/or direct effects on bone cells (Canalis et al., 2007) leading to induction of apoptosis in osteoblasts and osteocytes (Weinstein et al., 1998) and/or suppression of their differentiation. Whereas low doses of GCs stimulate (Shalhoub et al., 1992), high doses inhibit osteoblast differentiation, the latter being related to the inhibition of postconfluential proliferation (Smith et al., 2000). Suppression of osteoblast function could be a consequence of decreased expression of genes involved in bone formation, such as collagen type 1 (Col1a1) and Runt-related transcription factor 2 (Runx2), or could be due to antagonizing the bone morphogenetic protein (BMP) pathway and the Wnt signaling pathways (Canalis et al., 2007). Besides osteoblasts, modulation of osteoclast activity also appears to contribute to GC-induced osteoporosis (GIO). GCs induce the synthesis of receptor activator for nuclear factor-κB ligand (RANKL), an essential stimulator of osteoclastogenesis (Hofbauer et al., 1999). In addition, they prolong the longevity of osteoclasts in vivo, but decrease their bone degrading activity (Jia et al., 2006; Kim et al., 2006).

The majority of GC effects are mediated via the glucocorticoid receptor (GR), a widely expressed member of the nuclear receptor superfamily. Following hormone binding, the GR alters gene expression via several modes of action, including its binding as dimers to GC-responsive elements (GRE) present in the promoter of hormone-responsive genes and interaction of the monomeric receptor with DNA-bound transcription factors such as NF-KB, AP-1, IRF-3 or STAT5 (Kassel and Herrlich, 2007). Currently, suppression of these transcription factors is believed to underlie in part the anti-inflammatory effects of GCs, while dimerization of the GR is hypothesized to contribute to many of the side effects.

This view is supported by the finding that interaction with pro-inflammatory transcription factors is preserved in $GR^{dim}$ mice carrying a dimerization-deficient GR, while induction of GRE-dependent transcription is abolished (Reichardt et al., 1998; Reichardt et al., 2001). However, there is a requirement for GR dimerization to achieve full suppression of inflammation in contact allergy, septic shock and arthritis, as GC treatment is therapeutically inefficient in $GR^{dim}$ mice (Tuckermann et al., 2007) [Baschant et al. 2011, Kleiman et al. 2011].

The currently accepted paradigm regarding glucocorticoid therapy and GR activity is that in the absence of GC treatment, no GR-mediated gene regulation takes place, whereby AP-1 and NF-KB activity (amongst other transcription factors) leads to a profile of gene expression that induces an inflammatory response. During GC therapy GR function is altered, leading to GR-dimerization dependent gene activation, suggested to be involved in side effects, and GR-monomer dependent transrepression. In the latter case GR-dependent transcription factors such as NF-KB and AP-1 are repressed, therefore repressing the gene expression profile downstream of NF-KB and AP-1 that is associated with inflammation. It is thought that through the repression of NF-KB and AP-1 the anti-inflammatory effect of GC therapy is achieved. Both NF-KB and AP-1 have until now always been co-inhibited via GR during GC treatment. There have existed until now no compounds known to modulate NF-KB and AP-1 activities independently. Despite this effective anti-inflammatory treatment, the significant side effect of GC-induced osteoporosis (GIO) remains and until now remains poorly understood.

The publications and other materials, including patents, used herein to illustrate the invention and, in particular, to provide additional details respecting the practice are incorporated herein by reference in their entirety.

The present invention demonstrates that GR-mediated repression of AP-1 activity during GC therapy plays an important role in GIO. One of the important functions of AP-1 in preventing GIO is driving LIF expression, as shown in the examples below.

Leukaemia inhibitory factor (LIF) is a secreted polyfunctional cytokine which elicits a diversity of biological effects on many cell types. LIF expression has been detected in a variety of cell lines and primary tissues, including primordial germ cells, neurons, embryonic stem cells, adipocytes, hepatocytes and osteoblasts (reviewed Metcalf, 1992 (Growth Factors 7, 169-173); Heath, 1992 (Nature 359, 17)). The biological activities attributed to LIF are widespread. LIF stimulates T lymphocytes and monocytes, brain glial cells, liver fibroblasts, bone marrow stromal cells, thymic epithelial cells and uterine endometrial gland cells just prior to blastocyst implantation. However, until now there has been no mention of LIF in combination with a role in GIO.

The invention relates to agents and/or methods that selectively inhibit NF-KB through the GR, but have no inhibitory effect on AP-1 activity, or maintain or restore either AP-1 activity or one or more of the effects of AP1 activity, such as LIF expression, by maintaining LIF expression or by treatment with LIF.

These agents and/or methods therefore exhibit anti-inflammatory effects due to their NF-KB inhibitory effects but do not lead to GIO due to either an absence of AP-1 inhibitory activity or a restoration of AP-1 activity or maintenance or restoration of AP-1 mediated effects, by maintaining LIF expression or treatment with LIF.

Until now it was unknown that AP-1 or LIF played a role in GIO. It was also unknown that GR-transrepression could be influenced using particular agents to de-couple GR-mediated repression of NF-KB from AP-1 repression, therefore providing anti-inflammatory properties that do not simultaneously cause GIO.

Documents WO 2009/092796 A1 (compare U.S. Pat. No. 8,039,501) and WO 2003/073991 A2 (U.S. Pat. No. 7,655,420) mention the potential avoidance of GIO, although explain the avoidance of GC side effects by reciting the importance of compounds that do not lead to GR-transactivation. Neither disclosure reveals the inventive concept of the present invention; that NF-KB and AP-1 (or the down-stream effects of AP-1) should be differentially regulated in maintaining inflammatory properties that do not simultaneously cause GIO.

Further substances have been proposed in the prior art that are useful as anti-inflammatory compounds (WO 2009/058944 A2 (U.S. Pat. No. 8,309,730), WO 2006/076509 A1 (U.S. Pat. No. 7,317,024)), although such compounds do not exhibit the inventive properties of the present invention. Although AP-1 and LIF activity have been associated with bone-density, there has until now been no disclosure or suggestion that AP-1 or LIF play an important role in GC-induced osteoporosis.

Other approaches towards enhancing bone density, such as dexamethasone treatment, have no stimulatory effect on AP-1 at pharmacologically relevant doses (WO 2003/073991 A2 (U.S. Pat. No. 7,655,420), Kurahashi et al., 2005). As also described above, a stimulating effect for GCs on bone density has been previously described, however, at pharmacologically relevant doses GCs lead to the opposite effect, so that bone density is in fact reduced.

Compound A and its effect as an alternative to known glucocorticoids has been disclosed in the prior art (U.S. Pat. No. 7,053,120 B2, van Loo et al., 2010, Gossye et al., 2010, Wuest et al., 2009, Gossye et al., 2009, Zhang et al., 2009, Haegeman et al., 2006, De Bosscher et al., 2005). However, until the present time it was unknown that Compound A exhibits the inventive properties as described herein.

Other compounds have also been disclosed that could be of use in the treatment of GIO (WO 2004/106296 A2 (U.S. Pat. No. 7,459,460), WO 2004/106295 A2 (U.S. Pat. No. 7,265,145), WO 2005/077925 A1 (U.S. Pat. No. 7,820,702)). All such disclosures make however no mention of an effect on either AP-1 or GR.

SUMMARY OF THE INVENTION

The present invention provides, in certain aspects, agents and/or methods that exhibit anti-inflammatory activity but do not lead to GIO and methods for identifying such agents and/or methods.

In certain embodiments, the invention provides an agent and/or method that selectively inhibits NF-KB activity without inhibiting AP-1 activity.

In certain embodiments, the invention provides a method for the prophylactic and/or therapeutic treatment of glucocorticoid induced osteoporosis comprising inducing, maintaining or restoring AP-1 activity or one or more AP-1-mediated effects at therapeutically relevant levels, i.e., inducing, maintaining or restoring AP-1 activity or one or more AP-1-mediated effects to an level effective for treating glucocorticoid induced osteoporosis in a subject in need of said treatment.

In certain embodiments, the invention provides a method for the prophylactic and/or therapeutic treatment of glucocorticoid induced osteoporosis comprising the administration of leukemia inhibitory factor (LIF) or Interleukin-11 (IL-11), in particular, a therapeutically relevant, i.e. effective, amount of leukemia inhibitory factor (LIF) or Interleukin-11 (IL-11) to a subject. A method is also encompassed that comprises the administration of a therapeutically relevant, i.e. effective, amount of IL-11 or by inducing, maintaining or restoring IL-11 expression in a subject. A method is also encompassed that comprises the administration of LIF, in particular a therapeutically relevant, i.e. effective, amount of LIF or by inducing, maintaining or restoring LIF expression in a subject.

In certain embodiments, the invention provides methods that selectively inhibit NF-KB activity without inhibiting AP-1 activity, or methods that selectively inhibit NF-KB activity but provide restoration of AP-1 activity or maintenance or restoration of particular AP-1 mediated effects, such as maintaining LIF expression or direct treatment with LIF, or IL-11.

Certain embodiments disclosed herein have the object to provide a method for the prophylactic and/or therapeutic treatment of glucocorticoid induced osteoporosis comprising inducing, maintaining or restoring AP-1 activity or one or more AP-1-mediated effects at therapeutically relevant, i.e. effective, levels, wherein the method additionally comprises a method for the Prophylactic and/or therapeutic treatment of a medical condition associated with inflammation comprising inhibition of NF-KB activity.

In a preferred embodiment, the method is characterized in that the medical condition associated with inflammation is an allergy, autoimmune disease, arthritis or cancer.

In a preferred embodiment the method is characterized in that the subject is undergoing or has undergone glucocorticoid (GC) treatment. A method is also encompassed that is characterized in that the inhibition of NF-KB activity is GC treatment, comprising administration of a therapeutically relevant, i.e. effective, amount of GC.

In a preferred embodiment, the method is characterized in that the subject is undergoing or has undergone glucocorticoid treatment. In another embodiment, the method is characterized in that the treatment comprises simultaneous administration of LIF and glucocorticoid.

A subject undergoing GC treatment relates to any patient under a continuing regime of GC administration for any given disorder. A subject who has undergone such therapy is any patient who may have experienced any loss in bone density or other GIO effects due to past GC treatment. In order to find effects of GIO, bone mineral density tests (BMD) can be used, that show how dense bones are and whether osteoporosis is present. The most common osteoporosis test is dual X-ray absorptiometry—also called DXA or DEXA. Various other methods can check bone density, including ultrasound and quantitative computed tomography (QCT). Any patient who has previously received GC treatment and exhibits reduced bone density may be a relevant patient for the present therapeutic method.

Simultaneous treatment, otherwise known as co-treatment or joint treatment, may encompass the administration of separate formulations of GCs and LIF, wherein treatment may occur within minutes of each other, in the same hour, on the same day, in the same week or in the same month as one another. A combination medicament, comprising both LIF and GCs, may also be used in order to co-administer GCs and LIF in a single administration or dosage.

In one embodiment, the method is characterized in that the glucocorticoid-mediated suppression of osteoclast differentiation is reduced or alleviated. This feature represents a novel finding in comparison to known uses of LIF and was not necessarily inherently present uses of LIF. Due to the unique insights into the basis of GIO described herein, the effect on osteoclast differentiation represents a novel feature of the invention.

In one embodiment, the method is characterized in that the glucocorticoid is prednisolone. In one embodiment, the method is characterized in that the LIF is recombinant human LIF. Administration of a combination of recombinant human LIF with predisolone shows particularly beneficial effects, and shows good compatibility when co-administered in subjects, in particular showing reduced side effect profiles.

In one embodiment, the method is characterized in that the LIF is administered in the form of a pharmaceutical composition comprising a pharmaceutically acceptable carrier. In a preferred embodiment the pharmaceutically acceptable carrier is PLGA. The LIF-containing pharmaceutical composition may comprise of PLGA-based nanoparticles.

The invention also relates to a method for the prophylactic and/or therapeutic treatment of a medical condition associated with inflammation, such as allergies, autoimmune diseases, arthritis or cancer, comprising administration of GC to a subject, wherein the method additionally comprises a method for the Prophylactic and/or therapeutic treatment of glucocorticoid induced osteoporosis comprising the administration of a therapeutically relevant, i.e. effective, amount of LIF.

It was an entirely surprising development that the administration of LIF provided restoration of bone density after or during GC treatment and/or protection from osteoporosis in subjects receiving GC treatment. As is described in the experimental examples provided below (see especially FIG. 23 A, B, D), the administration of LIF counteracts GC-mediated loss in bone density and trabecular number. These results demonstrate the efficacy of separate and co-administration of GCs and LIF, in order to treat and/or prevent GC-induced osteoporosis.

The administration of LIF for counteracting GIO represents an additional and distinct technical effect when compared to the use of LIF in the treatment of osteoporosis as such. GIO is mechanistically directly related to AP-1 and LIF function, as is shown herein, due to the physical and/or mechanistic interaction between the GR and AP-1 gene elements. GIO is a particular form of osteoporosis characterised by a distinct mechanism, which is directly related to AP-1 and LIF function, as disclosed herein. The treatment of GIO using LIF is therefore based directly on novel mechanistic insights into the GIO disease, and comprises a novel technical effect not inherent in the administration of LIF in the treatment of osteoporosis as such.

The administration of LIF therefore also represents a potential solution to a long-felt-need in the field for avoiding such a debilitating side effect (GIO) of an otherwise successful treatment for inflammation (GC administration).

Until now there has been no disclosure of agents or methods that selectively inhibit NF-KB without inhibiting AP-1, in particular in osteoblasts. GC-compounds known in the art have previously exhibited an effect of transrepression of both NF-KB and AP-1, thereby providing an anti-inflammatory effect but also causing GIO. The present invention contributes the surprising and novel concept that NF-KB inhibition plays an important role in anti-inflammatory effect of GCs, whereby the maintenance of AP-1 activity plays an important role in avoiding and/or treating GIO. Compounds and methods that exhibit properties leading to differentially regulated NF-KB and AP-1, such as described herein, have until now been neither suggested nor disclosed in the prior art.

The invention also relates to an agent and/or method that disrupts glucocorticoid receptor (GR) function, preferably by binding to GR, characterized in that NF-KB function is inhibited and AP-1, LIF or IL-11 activity is induced, maintained or restored at normal levels and/or levels normal in a subject not undergoing glucocorticoid (GC) therapy, i.e. levels that exist in a subject not undergoing glucocorticoid (GC) therapy, for use as a medicament.

Therefore, in one embodiment the agent of the present invention is characterised in that the agent is a GR-Ligand. In a preferred embodiment the agent of the present invention is a GR-Ligand that modulates GR activity, so that the repressive function of GR on AP-1 during GC treatment is alleviated.

In a preferred embodiment the agent and/or method of the present invention is intended for use in the therapeutic and/or prophylactic treatment of a medical condition associated with inflammation, such as allergies, autoimmune diseases, arthritis or cancer, characterized in that glucocorticoid-induced osteoporosis (GIO) is inhibited and/or suppressed.

In a preferred embodiment the agent and/or methods of the present invention is intended for use in the therapeutic and/or prophylactic treatment of glucocorticoid-induced osteoporosis (GIO), preferably in a patient undergoing glucocorticoid treatment.

In one embodiment the method of the present invention is characterised in that the method comprises administration of a glucocorticoid or glucocorticoid derivative.

In one embodiment the method of the present invention is characterised in that a therapeutically relevant, i.e. effective, amount of an AP-1 agonist is administered.

In one embodiment the method of the present invention is characterised in that the method comprises administration of a therapeutically relevant, i.e. effective, amount of an NF-KB inhibitor.

The invention also encompasses administration of an agent that inhibits NF-KB function without inhibition of AP-1 activity. In one embodiment the method of the present invention is characterised in that the agent is Compound A

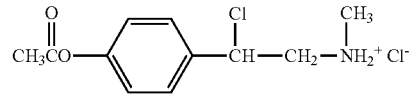

or a derivative thereof.

Various derivatives are known in the art of Compound A. These derivatives, in regards to those that exhibit the same functional properties of Compound A as described herein, also fall under the scope of the present invention.

Even though Compound A has been disclosed as exhibiting anti-inflammatory activity, there has been no disclosure of Compound A in relation to GIO. The use of Compound A in the treatment of GIO represents a new use of a known compound.

The medical use of treating GIO and of GIO-avoidance (prophylaxis/prevention) opens new groups and patient collectives that can be treated with Compound A and the methods of the present invention, such as patients who require GC therapy but are sensitive to osteoporosis, or those patients who have osteoporosis and require GC-like therapies. The treatment of such patients has been up until now difficult, if not impossible, due to the side effects of traditional GC compounds.

In a preferred embodiment the agent and/or method of the present invention is characterised in that inhibition of NF-KB activity and maintenance of AP-1 activity, or restoration of AP-1 activity or maintenance or restoration of AP-1 mediated effects, by maintaining LIF expression or direct treatment with LIF, occurs in bones and/or osteoblasts.

The invention therefore also relates to methods that comprise the use of agents that selectively inhibit NF-KB activity without inhibiting AP-1 activity in cells of the osteoblasts lineage, whereby AP-1 activity can be inhibited in cells of other lineages. Experiments show that the AP-1 dependent gene MMP-13 is repressed in monocytic cells after Compound A treatment, thereby indicating that in a preferred embodiment of the invention the absence of AP-1 inhibition occurs primarily in cells of the osteoblasts lineage, although not necessarily in other cell lineages.

In a preferred embodiment the agent and/or method of the present invention is characterised in that osteoblast function and/or osteoblast differentiation is induced, maintained or restored at normal levels and/or levels normal in a subject not undergoing GC therapy.

In one embodiment the agent and/or method of the present invention is characterised in that osteoclast differentiation is suppressed.

In one embodiment the agent and/or method of the present invention is characterised in that GR receptor dimerisation is inhibited.

In one embodiment the agent and/or method of the present invention is characterised in that expression of the IL-11 and/or leukemia inhibitory factor (LIF) genes or the activity of IL-11 and/or leukemia inhibitory factor (LIF) proteins are induced, maintained or restored at normal levels and/or levels normal in a subject not undergoing GC therapy.

In one embodiment the agent and/or method of the present invention is characterised in that the binding of or physical interaction between GR and AP-1 proteins and/or GR and the AP-1 binding sites in the promoter of the IL-11 and/or LIF genes is inhibited. In this sense the agent (or agents) applied in the method need not necessarily be a GR-Ligand as commonly understood, but rather an agent that prevents GR binding to AP-1 binding sites in the promoter regions of AP-1 dependent genes. For example an agent such as an antibody could be applied to disrupt GR-AP-1 interaction, thereby allowing administration of NFKB inhibitors that would usually lead to GR-mediated effects on AP-1, in combination with such agents or antibodies that disrupt GR-AP-1 interaction, which would thereby lead to the desired NFKB inhibition without the undesired GR-mediated effects on AP-1. Alternatively the gene products of AP-1 dependent genes may be additionally administered directly, or through other therapeutic approaches such as via gene therapy. One embodiment of such a method is the administration of LIF, which is an AP-1 dependent gene product.

Such an agent and/or method would therefore be useful in application in combination with traditional GC or other comparable GR-binding agents or drugs. The agent and/or method of the present invention can be used in combination therapy with classical GC compounds, such as those currently known in the art. Therefore the administration of a common or traditional GC compound can be accompanied by administration of the AP-1 dependent gene product, such as LIF, thereby enabling NF-KB inhibition via GC administration, without the detrimental effect inherent in AP-1 inhibition, via LIF administration. The administration of LIF thereby counteracts and compensates for the detrimental AP-1 inhibition caused by GC treatment.

In a preferred embodiment an agent and/or method that disrupts the physical interaction between GR and the AP-1 binding sites in the promoter of the IL-11 and/or LIF genes is to be used in combination with other GC compounds during therapy. Such an agent and/or method preferably blocks the GR-transrepression effect on AP-1 in osteoblasts, especially when in combination therapy with other GC compounds, so that GIO is prevented.

Such an approach also relates to the method of treatment disclosed in the present invention, whereby NF-KB is inhibited and AP-1 activity is maintained. Alternatively, restoration of AP-1 activity or maintenance or restoration of AP-1 mediated effects can be maintained by allowing either LIF expression or providing direct treatment with LIF. Such a method may include the administration of separate agents, one that inhibits NF-KB and one that leads to maintenance of AP-1 activity, preferably during GC therapy. In this context the maintenance of AP-1 activity refers also to restoration of AP-1 activity or maintenance or restoration of AP-1 mediated effects. A preferred embodiment is direct treatment with LIF, which represents the restoration or compensation of an AP-1 mediated effect.

The invention further relates to the use of an agent as described herein as a medicament and/or a method for therapeutic and/or prophylactic treatment of a medical condition associated with inflammation, such as allergies, autoimmune diseases, arthritis or cancer, characterized in that glucocorticoid-induced osteoporosis (GIO) is inhibited and/or suppressed.

The invention further relates to the use of AP-1 and/or AP-1 dependent genes or gene products, such as LIF, as targets or active agents for the modulation of osteoblast function and/or differentiation.

The invention further relates to the use of IL-11 for therapeutic and/or prophylactic treatment of glucocorticoid-induced osteoporosis (GIO), preferably in a patient undergoing glucocorticoid treatment. There has been minor mention of using IL-11 for treating osteoporosis in the prior art (EP0835128B1 (compare U.S. Pat. No. 5,679,339), U.S. Pat. No. 6,998,123; U.S. Pat. No. 6,846,907), although there has until now been no disclosure of the use of IL-11 for the treatment and/or prevention of GIO.

The invention further relates to the use of LIF for therapeutic and/or prophylactic treatment of glucocorticoid-induced osteoporosis (GIO), preferably in a patient undergoing glucocorticoid treatment.

The invention further relates to Compound A for use as a medicament for therapeutic and/or prophylactic treatment of a medical condition associated with inflammation, such as allergies, autoimmune diseases, arthritis or cancer, characterized in that glucocorticoid-induced osteoporosis (GIO) is inhibited and/or suppressed.

The invention also relates to a method for identifying an agent as described herein, or for identifying a method that exhibits the desired characteristics as described herein, namely selectively inhibiting NF-KB activity without inhibiting AP-1 activity, or maintaining AP-1 activity or the effects of AP1 activity.

In a preferred embodiment the method is characterised in that

IL-6 and/or CXCL10 expression is measured and compared between cultured mammalian cells treated with or without the agent to be tested, whereby suppression of IL-6 and/or CXCL10 expression in the treated cells indicates NF-KB inhibition by said agent, and/or ALP activity and/or LIF and/or IL-11 expression and/or activity is measured and compared between cultured mammalian cells treated with or without the agent to be tested, whereby a reduction of ALP activity and/or a reduction of LIF and/or IL-11 expression and/or activity in the treated cells indicates inhibition of AP-1 activity by said agent.

The invention also relates to a method, preferably as described above, for identifying an agent, preferably as described above, which selectively inhibits NF-KB activity without inhibiting AP-1 activity, whereby the agent to be identified exhibits anti-inflammatory activity and does not inhibit osteoblast differentiation, characterised in that IL-6 and/or CXCL10 expression is measured and compared between cultured mammalian cells treated with or without the agent to be tested, whereby suppression of IL-6 and/or CXCL10 expression in the treated cells indicates NF-KB inhibition and anti-inflammatory activity by said agent, and/or ALP activity and/or LIF and/or IL-11 expression is measured and compared between cultured mammalian cells treated with or without the agent to be tested, whereby a reduction of ALP activity and/or a reduction of LIF and/or IL-11 expression in the treated cells indicates inhibition of AP-1 activity by said agent.

In another embodiment the method as described herein can be described in terms of the absence of reduction in ALP activity and/or LIF and/or IL-11 expression, whereby ALP activity and/or LIF and/or IL-11 expression is measured and compared between cultured mammalian cells treated with or without the agent to be tested, whereby no reduction of ALP activity and/or no reduction of LIF and/or IL-11 expression in the treated cells indicates no inhibition of AP-1 activity and no inhibitory effect on osteoblasts differentiation by said agent.

In one embodiment the method for identifying an agent that exhibits anti-inflammatory activity and does not inhibit osteoblast differentiation is characterized in that TNF-alpha production is measured and compared between cultured mammalian cells treated with or without the agent to be tested, whereby suppression of TNF-alpha production in the treated cells indicates anti-inflammatory activity of said agent.

In one embodiment the method as described herein is characterised in that the agent to be identified additionally inhibits binding of or physical interaction between GR and the AP-1 binding sites in the promoter of the IL-11 and/or LIF genes, characterized in that chromatin-immunoprecipitation (ChIP) is carried out using cultured mammalian cells treated with or without the agent to be tested, preferably using an antibody against GR and PCR amplification of the AP-1 binding site(s) in the promoter of the IL-11 and/or LIF genes.

The method for identifying an agent with the inventive properties as described herein can be carried out using either manual or automated approaches. There are numerous experimental approaches provided throughout the disclosure of the present application, each of which are capable of being carried out manually, for example using small scale approaches with individual laboratory protocols, or in an automated fashion. The automated identification method can be carried out in a large scale, high-throughput manner, which is capable of testing chemical libraries, such as those containing compound A derivatives, other small molecules or RNAi libraries. The automation of such a method is preferred in that automated high throughput microscopy is applied (such as immunofluorescence microscopy), whereby mammalian cells in vitro are treated with any number of compounds to be tested, thereby identifying the agents that exhibit the properties as described herein using the experimental criteria provided herein, especially those in the experimental examples provided herein.

The invention further relates to a kit for carrying out the method for identifying an agent or a method as described herein, which selectively inhibits NF-KB activity without inhibiting AP-1 activity, or maintaining AP-1 activity or the effects of AP1 activity, comprising means for carrying out the experimental procedures described herein, preferably in an automated fashion, and more preferably for carrying out the testing of antisense molecules, such as libraries of RNAi molecules, and/or libraries of small molecules.

In one embodiment of the present invention the method further comprises of preparation of the agent that is identified in a pharmaceutical composition for medical administration by combining said agent with at least one pharmaceutically acceptable carrier.

The invention further relates to a pharmaceutical composition comprising the agent identified by the method as described above for use as a medicament for therapeutic and/or prophylactic treatment of a medical condition associated with inflammation, such as allergies, autoimmune diseases, arthritis or cancer, whereby glucocorticoid-induced osteoporosis (GIO) is inhibited and/or suppressed.

The invention further relates to a pharmaceutical composition comprising the agent as described herein with a pharmaceutically acceptable carrier.

The invention also relates to a method of therapeutic and/or prophylactic treatment of a medical condition associated with inflammation, such as allergies, autoimmune diseases, arthritis or cancer, comprising administration of a therapeutically effective amount of the agent as described herein, such as either a compound that selectively inhibits NF-KB activity without inhibiting AP-1 activity, or administration of a common (traditional) GC compound in combination with the maintenance of AP-1 activity via treatment with LIF, and/or administration of the pharmaceutical compound as described herein to a subject, characterized in that glucocorticoid-induced osteoporosis (GIO) is inhibited and/or suppressed. Inhibition or suppression of GIO is therefore facilitated by the compound itself, which selectively inhibits NF-KB activity without inhibiting AP-1 activity, or in the case of a traditional GC compound, by additional treatment with an AP-1-dependent gene product, most preferred LIF.

The invention further relates to a method of therapeutic and/or prophylactic treatment of glucocorticoid-induced osteoporosis (GIO), preferably in a patient undergoing glucocorticoid treatment, comprising administration of a therapeutically effective amount of the agent as described herein, such as either a common (traditional) GC compound or a compound that selectively inhibits NF-KB activity without inhibiting AP-1 activity, and/or the pharmaceutical compound as described herein to a subject and that glucocorticoid-induced osteoporosis (GIO) is inhibited and/or suppressed. Inhibition or suppression of GIO is therefore facilitated by the compound itself, which selectively inhibits NF-KB activity without inhibiting AP-1 activity, or in the case of a traditional GC compound by additional treatment with an AP-1-dependent gene product, most preferred LIF.

The invention further relates to a method of selectively inhibiting NF-KB activity without inhibiting AP-1 activity for the therapeutic and/or prophylactic treatment of a medical condition associated with inflammation, such as allergies, autoimmune diseases, arthritis or cancer, whereby glucocorticoid-induced osteoporosis (GIO) is inhibited and/or suppressed.

The invention further relates to a method of selectively inhibiting NF-KB activity without inhibiting AP-1 activity for the therapeutic and/or prophylactic treatment of glucocorticoid-induced osteoporosis (GIO), preferably in a patient undergoing glucocorticoid treatment.

The invention further relates to AP-1 activity as a target for the therapeutic and/or prophylactic treatment of glucocorticoid-induced osteoporosis (GIO), preferably in a patient undergoing glucocorticoid treatment.

BRIEF DESCRIPTION OF THE FIGURES

FIG. 15. Bone geometry of 10 weeks old $GR^{flox}$ and $GR^{Runx2Cre}$ mice. Data shown as mean±SD. * $p<0.05$; ** $p<0.01$ (n=5-6).

FIG. 16. Bone geometry of 10 weeks old wild type and $GR^{dim}$ mice. Data shown as mean±SD. * $p<0.05$; ** $p<0.01$ (n=5-6).

ELISA was used to measure protein levels of Interleukins 6 (IL-6) and 8 (IL-8) in the supernatant collected from the cells. (n=3; * p<0.05, ** p<0.01; One-way ANOVA, followed by a Dunnett's Multiple Comparison Test; Hypoxanthine-guanine phosphoribosyltransferase (HPRT) was used for normalization)

Figure 21:
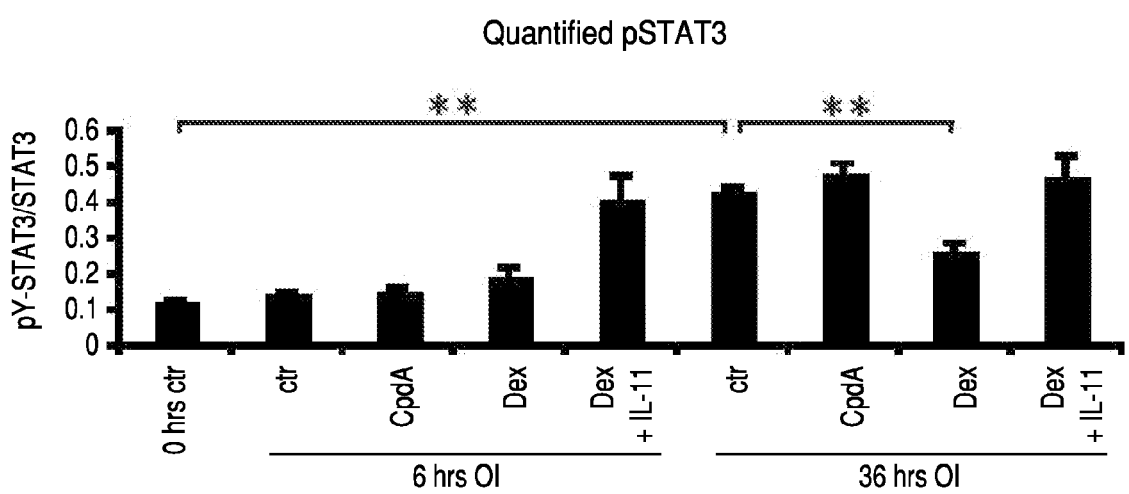

FIG. 21. Quantification of Western Blot analysis of phosphorylated STAT3 levels in primary osteoblasts. Cells were treated for 6 or 36 hrs with $10^{-6}$ M Dex, $10^{-6}$ M Dex plus 5 ng/ml IL-11 or $10^{-6}$ M CpdA under osteogenic conditions (OI) in comparison to cells in control medium (ctr). Quantification of Western Blot intensity of pTyrSTAT3 is shown versus total STAT3 from D (n=4; ** p <0.01, One-way ANOVA, followed by a Dunnett's Multiple Comparison Test)).

Figure 22:
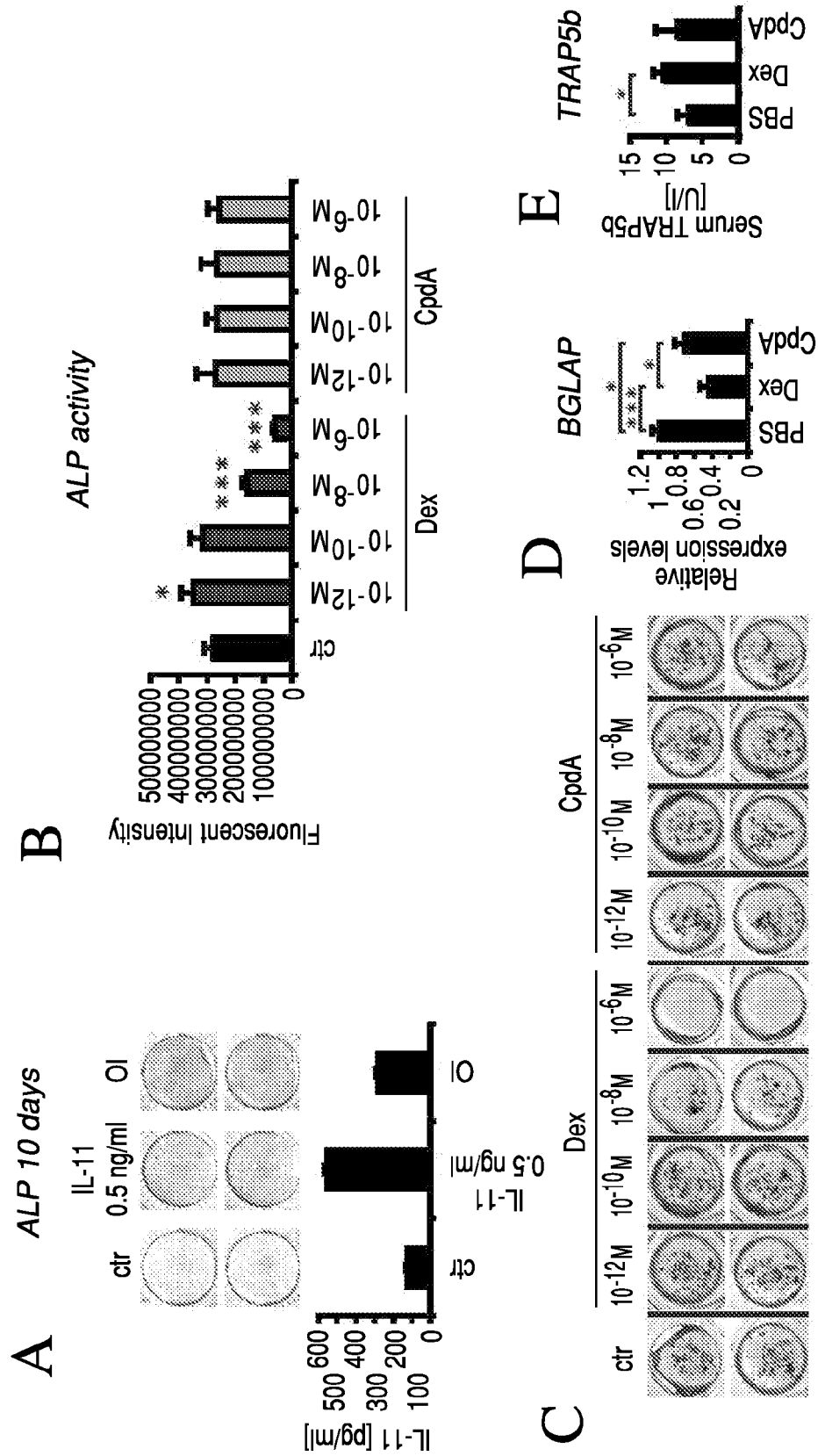

FIG. 22. Determination of alkaline phosphatase activity (ALP) and corresponding IL-11 levels with ELISA 48 hrs after induction. A) Primary osteoblasts of wild type mice were cultured for 10 days with osteogenic inducers (OI) or 0.5 ng/ml IL-11 compared to untreated cells (ctr). Cells were fixed and stained for alkaline phosphatase activity (ALP). The corresponding IL-11 levels were determined with ELISA 48 hrs after induction. B, C) Primary osteoblasts of wild-type (wt) and $GR^{null}$ mice were subjected to OI differentiation during treatment with Dex or CpdA at indicated doses. ALP activity was quantitatively determined by automated microscopy of ELF® stained cultures or (B) qualitatively after classical ALP staining C, D, E) DBA/1 mice were treated daily with Dex (62.5 ug), CpdA (300 ug), or solvent (PBS) for 8 d. Serum was collected according to standard procedures, and ELISA was performed for the measurement of osteocalcin levels (D) and TRAP5b levels (E) (n=5 for PBS; n=6 for CpdA; n=7 for Dex). *P<0.05, **P<0.01; Kruskal-Wallis test followed by Dunn's multiple comparison test.

Figure 23:
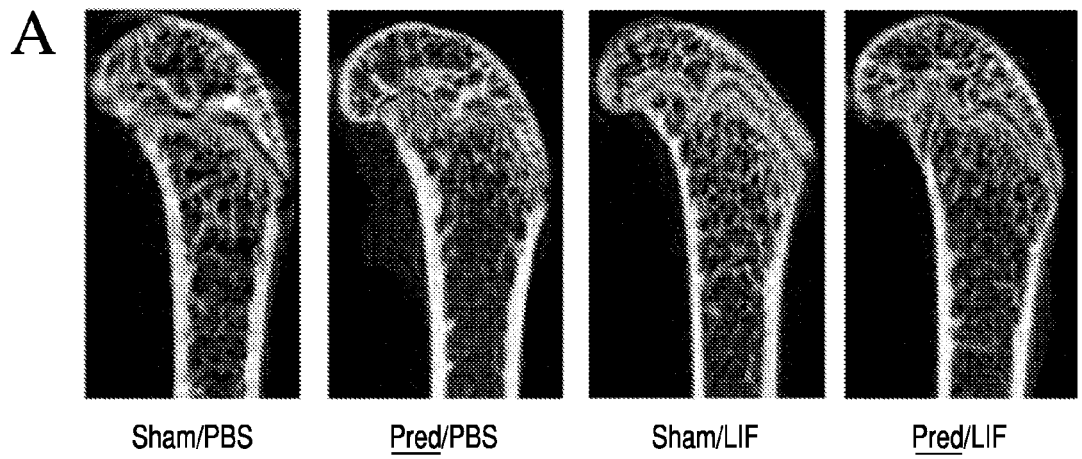
Figure 23:
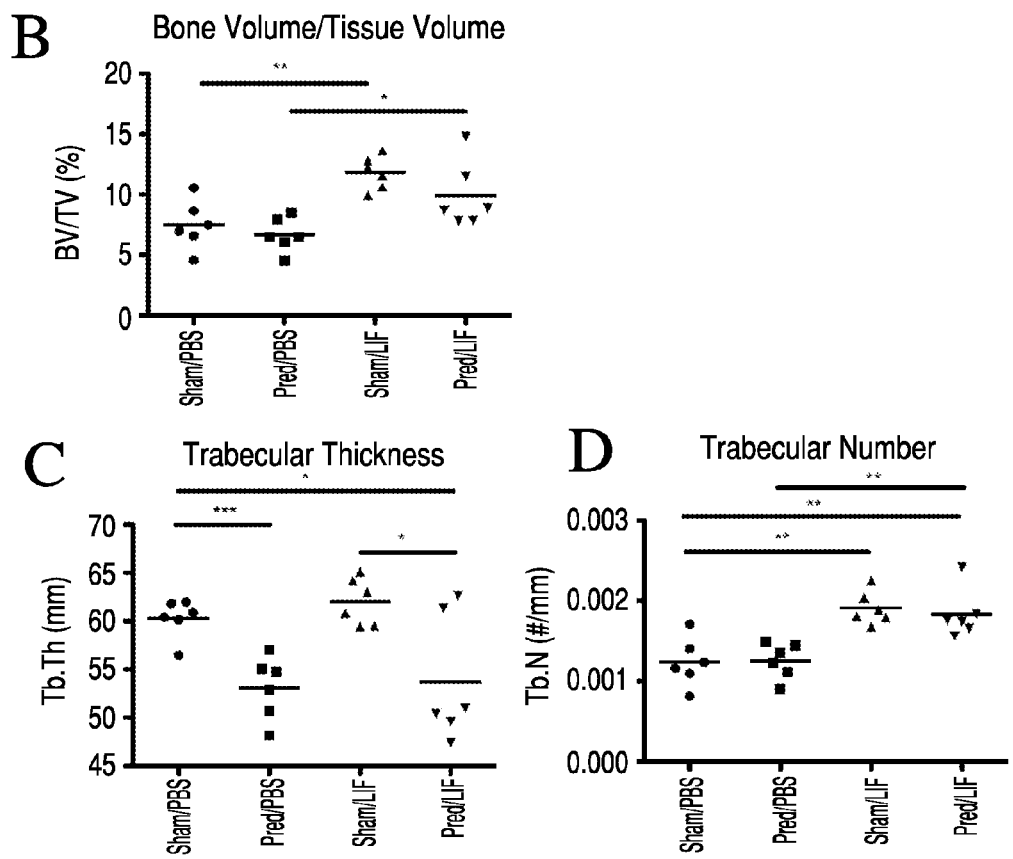

FIG. 23. LIF treatment elevates bone density of prednisolone treated mice. Female 9 week old FVB/N mice were treated with control pellets (sham), prednisolone (Pred) releasing pellets (12 mg/kg/day releasing rate) and were treated one day later with PBS and LIF i.p. injections twice a day (0.2 mg/kg/day) until 15 days. Mice were sacrificed on day 16. MicroCT Analysis was performed and representative longitudinal sections shown in (A), Bone Volume/Tissue volume determined (B) and trabecular thickness and trabecular numbers calculated (C, D). n=6, * p<0.05,  p<0.01, * p<0.001

DETAILED DESCRIPTION OF VARIOUS AND PREFERRED EMBODIMENTS OF THE INVENTION

The "agent" of the present invention relates preferably to any agent, compound or substance that exhibits the properties described herein.

The term "inhibition of NF-KB activity" refers to an inhibitive effect on NF-KB as commonly understood by one skilled in the art, preferably so that genes, whose expression depends on NF-KB activity (such as IL-6 and CXCL10), are not expressed to the level which would normally occur without treatment of the agent described herein, or preferably that genes normally repressed by NF-KB activity are not repressed as would normally occur without treatment of the agent described herein. In a preferred embodiment NF-KB inhibition relates to GC-activation of the GR, which in turn leads to NF-KB inhibition. Inhibition relates in general to any reduction of activity of NF-KB genes or proteins, regarding expression of all NF-KB family members themselves, down-regulation of NF-KB protein activities or transcription factor activities. NF-KB activity can be tested by one skilled in the art, preferably using the methods disclosed herein.

AP-1 is a transcription factor responsible for the expression of multiple genes. "AP-1-mediated effects" therefore relate to the expression and/or activity of AP-1 dependent genes leading to functional effects at nucleic acid or protein level. Maintaining or restoring one or more AP-1-mediated effects may also relate to administration of an AP-1-dependent gene (DNA) or gene product (RNA or protein) without directly modulating AP-1 activity. Examples of AP-1-mediated effects are LIF and/or IL-11 expression and/or activity. The levels of expression or activity of AP-1-dependent genes or gene products, such as LIF or IL-11, can be easily determined by a skilled person using common techniques, such as expression profiling using microarrays, sequencing technologies or quantitative or Real-Time-PCR for determining nucleic acid levels, or by using protein-based assays, such as western blot, or ELISA, or activity-based assays, to determine levels of AP-1-dependent proteins The term "without inhibiting AP-1" refers to the absence of inhibitory effect on AP-1 activity, and/or activities of c-Jun (c-Jun, JunB, JunD), c-Fos (FosB, Fra1, Fra2), ATF (ATFa, ATF2, ATF3, B-ATF) and/or MAF protein family (NFIL6) members as commonly understood by one skilled in the art, so that preferably the functional properties of the agents as described herein are such that no significant inhibitive effect on AP-1 activity occurs, so that AP-1 activity or one or more specific effects of AP-1 activity, such as LIF expression or LIF activity (also via administration of LIF), is maintained or restored to normal levels, for example at levels normal in a subject (or in mammalian cell culture) not undergoing glucocorticoid (GC) treatment. The term "without inhibiting AP-1" therefore also relates to the induction, maintenance or restoration of AP-1 activity or to the induction, maintenance or restoration of one or more AP-1-mediated effects, such as administration of proteins or gene products that are dependent on AP-1 activity. In particular this relates to methods comprising the administration of LIF or IL-11, thereby providing a product of AP-1 function. Although AP-1 may itself be inhibited, for example by GR-mediated effects caused by GC treatment, the restoration or maintenance of one or more AP-1 dependent effects, such as LIF activity or expression, for example by administration of LIF, is also encompassed in the term "without inhibiting AP-1".

AP-1 activity can be tested by one skilled in the art, preferably using the methods disclosed herein. The terms used herein with regard to AP-1 activity also relate to c-Jun- and/or c-Fos-family members activity. Within the AP-1 complex, c-Jun, c-Fos, ATF and/or MAF protein family members interact with one another to form a dimer and therefore share related activities. Therefore, "AP-1 activity" according to the present invention can preferably be understood as additionally "Jun family member activity" and/or "Fos member activity" and/or "ATF member" activity and/or "MAF member activity". The c-Jun/c-Fos dimeric AP-1 complexes are those most affected by the GR, and are therefore in a preferred embodiment the AP-1 complexes that are not inhibited by the agents of the present invention.

The term "GR disruption" refers to modulation or disruption of GR function, preferably in that the GR-mediated suppression of NF-KB activity is maintained by treatment of the agent according to the present invention but that there is no GR-mediated repression of AP-1, which commonly occurs during GC-therapy. NF-KB inhibition may also be achieved by agents that directly inhibit NFKB without a GC-mediated effect.

Examples of agents of the present invention that can be used in the methods described herein include, but are not limited to: LIF, AP-1, c-Jun and/or c-Fos polypeptides, peptides, peptidomimetics or functional fragments thereof; nucleic acids which encode a LIF, AP-1, c-Jun and/or c-Fos polypeptide or functional fragments thereof, agents which increase the expression of endogenous LIF, AP-1, c-Jun and/or c-Fos, e.g., an agent which increases transcription of LIF, AP-1, c-Jun and/or c-Fos, small molecules which bind to GR, LIF, AP-1, c-Jun and/or c-Fos molecules and modulate their activity, such as agonist anti-LIF molecules, anti-AP-1 antibody molecules, agonist anti-c-Jun antibody molecules and agonist anti-c-Fos antibody molecules. Antibody modulators of GR are also included in the scope of the present invention.

Examples of small molecules include, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organomettallic compounds). Oligonucleotides that either code for and enhance production of LIF, AP-1, c-Jun and/or c-Fos molecules are encompassed in the invention in addition to antisense nucleotides that recognise NF-KB sequences, resulting in reduction and/or inhibition of NF-KB function without inhibiting LIF, AP-1, c-Jun and/or c-Fos function. RNAi based approaches using antisense nucleic acids that modulate activity and/or expression of the target molecules disclosed herein, preferably GR, LIF, AP-1, c-Jun, c-Fos and/or NF-KB, are included in the scope of the present invention. Such approaches are known to those skilled in the art and can be carried out based on the disclosure of the present invention included herein.

By "LIF" and/or "LIF-like polypeptides" is meant derivatives and homologues of LIF and extends to the entire natural length LIF molecule or derivatives thereof carrying single or multiple amino acid substitutions, deletions and/or additions and includes substitution, deletion and/or addition of any other molecules associated with LIF and its derivatives such as, inter alia, carbohydrate, lipid and polypeptide moieties, provided said derivatives retain sufficient activity to be useful in the practice of the present invention. LIF-like polypeptides extend to molecules having substantially similar activity as LIF while carrying amino acid rearrangements or alterations. The preparation of various derivatives of LIF will be apparent from the disclosure in PCT/AU88/00093 of the recombinant LIF molecule and its corresponding DNA. Additionally, molecules inducing LIF receptor activity and the common receptor GP 130 are encompassed in the present invention. Such effects and molecules relate to the same invention and can be used in the methods described herein. In various cases the means for administering LIF or for inducing LIF or LIF-receptor activity may well be, as such, known in the art, however their use in the methods of the present invention including their use in the treatment of the medical conditions described herein, have until now not been described.

Reference herein to LIF encompasses LIF-like polypeptides and fragments of LIF, and vice versa.

Hence, the present invention extends to naturally occurring but substantially pure LIF (i.e. greater than or equal to 70% by weight of LIF relative to other proteins or molecules and preferably greater than or equal to 85% and even more preferably greater than or equal to 90%), to recombinant LIF and to synthetic LIF made, for example, by chemical means.

Depending on the animal to be treated or the disease state to be treated, LIF may be from a range of sources such as, but not limited to, human, mouse, dog, cow, pig, sheep or other ruminant. In some cases it will be preferable to use homologous LIF to the animal being treated, for example, human LIF on humans. But in other circumstances, heterologous LIF may be more convenient and/or more effective. The choice of source of LIF may depend on the exigency of the treatment required or the animal requiring treatment.

In one embodiment of the subject invention, LIF and/or LIF-like polypeptides are used alone. In another embodiment, they are used in a combination with one or more other cytokines, which affect various aspects of bone resorption, bone formation and/or avoidance of GIO. The present invention also extends to the use of LIF and/or LIF-like polypeptides in combination with other active molecules such as agonists, antagonists, calcium or any inorganic or organic molecule which aid in the bone resorbing and/or forming process or in the avoidance of GIO, either directly or by enhancing the effect of LIF or LIF-like polypeptides.

Both human and mouse LIF cDNAs encode mature LIF polypeptides of 180 amino acid residues with a predicted molecular mass of approximately 20 kDa. Various isoforms of LIF are known and are also included in the scope of the invention. The mature form of the LIF protein is present as a monomer in solution. In eukaryotic cells LIF is subjected to extensive post-translational glycosylation. Native human and mouse LIF can be highly glycosylated (Moreau et al., 1988, (Nature 336, 690-692); Smith et al., 1988 (Nature 336, 688-690)), single chain molecules varying in molecular masses from approximately 38-67 kDa. Both human and murine LIFs have multiple N- and O-linked glycosylation sites and six conserved cysteine residues that are involved in three intramolecular disulfide bridges. The non-glycosylated, *E. coli*-expressed, recombinant human LIF is indistinguishable from native LIF in its biological activities in vitro. Human and murine mature LIF exhibit a 78% sequence identity at the amino acid level, whereas human LIF is equally active on both human and mouse cells, murine LIF is approximately 1000 times less active on human cells.

Mammalian homologues or fragments thereof of LIF which have the alterations mentioned above in the corresponding residues of their sequences may also be used in the present invention. Such homologues can be obtained by routine cloning procedures, e.g. by using the hLIF cDNA sequence as a probe to obtain another mammalian LIF from a cDNA library made from cells of the mammal which express LIF. The human and mammalian LIF proteins may be altered using standard techniques of genetic engineering known per se (e.g. see Sambrook et al (Molecular Cloning: A Laboratory Manual, 1989) and which are further illustrated in the examples below.

The invention further provides a recombinant protein or fragment thereof which comprises a site (as defined above) from LIF or a variant thereof. For example, the recombinant protein may comprise a protein or fragment thereof of the invention which further comprises, at the N- or C-terminus, all or part of the sequence of a cytokine including a cytokine selected from the group consisting of murine LIF.

The LIF may be administered using PLGA or poly(lactic-co-glycolic acid), which is a copolymer used in a host of Food and Drug Administration (FDA) approved therapeutic devices, owing to its biodegradability and biocompatibility. PLGA is synthesized by means of random ring-opening co-polymerization of two different monomers, the cyclic dimers (1,4-dioxane-2,5-diones) of glycolic acid and lactic acid.

Depending on the ratio of lactide to glycolide used for the polymerization, different forms of PLGA can be obtained. PLGA degrades by hydrolysis of its ester linkages in the presence of water. It has been shown that the time required for degradation of PLGA is related to the monomers' ratio used in production: the higher the content of glycolide units, the lower the time required for degradation. These properties allow tailoring of the carrier PLGA to enable release rates of the LIF appropriate for the treatment described herein.

PLGA has been successful as a biodegradable polymer because it undergoes hydrolysis in the body to produce the original monomers, lactic acid and glycolic acid. These two monomers under normal physiological conditions, are by-products of various metabolic pathways in the body. Since the body effectively deals with the two monomers, there is minimal systemic toxicity associated with using PLGA for drug delivery or biomaterial applications. The possibility to tailor the polymer degradation time by altering the ratio of the monomers used during synthesis has made PLGA a common choice in the production of a variety of chemical carrier systems such as micro and nanoparticles. Applications of PLGA in combination with LIF are known and may be suitable for the present invention (Park, J. et al. Modulation of CD4+ T lymphocyte lineage outcomes with targeted, nanoparticle-mediated cytokine delivery. Mol. Pharm. 8, 143-152 (2011)). PLGA carrier systems provide protection from LIF degradation in vivo, thereby allowing effective treatment via prolonged effective administration times.

Glucocorticoids (GC) are a class of steroid hormones that bind to the glucocorticoid receptor (GR), which is present in almost every vertebrate animal cell. GCs are part of the feedback mechanism in the immune system that turns immune activity (inflammation) down. They are therefore used in medicine to treat diseases caused by an overactive immune system, such as allergies, asthma, autoimmune diseases and sepsis. GCs have many diverse (pleiotropic) effects, including potentially harmful side effects. They also interfere with some of the abnormal mechanisms in cancer cells, so they are used in high doses to treat cancer. This includes mainly inhibitory effects on lymphocyte proliferation (treatment of lymphomas and leukaemias) and mitigation of side effects of anticancer drugs. GCs cause their effects by binding to the glucocorticoid receptor (GR). The activated GR complex, in turn, up-regulates the expression of anti-inflammatory proteins in the nucleus (a process known as transactivation) and represses the expression of proinflammatory proteins in the cytosol by preventing the translocation of other transcription factors from the cytosol into the nucleus (transrepression). GCs may include Hydrocortisone (cortisol), Cortisone, Prednisone, Prednisolone, Methylprednisolone, Dexamethasone, Betamethasone, Triamcinolone, Beclometasone, Fludrocortisone acetate or Deoxycorticosterone acetate (DOCA).

The term osteoporosis is to be understood as a disease of bones that leads to an increased risk of fracture. In osteoporosis, the bone mineral density (BMD) is reduced, bone microarchitecture deteriorates, and/or the amount and variety of proteins in bone are altered. Osteoporosis is defined by the World Health Organization (WHO) as a bone mineral density of 2.5 standard deviations or more below the mean peak bone mass (average of young, healthy adults) as measured by dual-energy X-ray absorptiometry. This definition may be applied in determining osteoporosis, however any reduction in bone density may also be viewed as osteoporosis. Prolonged use of medications such as glucocorticoids can induce the disease steroid- or glucocorticoid-induced osteoporosis.

Glucocorticoid-induced (or steroid-induced) osteoporosis (GIO) is osteoporosis arising due to use of glucocorticoids. The synthetic glucocorticoid prescription drug prednisone shows this effect after prolonged intake. Mechanisms of GIO include direct inhibition of osteoblast function, direct enhancement of bone resorption, inhibition of gastrointestinal calcium absorption, increased urine calcium loss and/or inhibition of sex steroids.

The term "medical condition associated with inflammation" refers to any medical condition, disorder or disease related to inflammation, such as allergies, autoimmune diseases, arthritis or cancer. The therapeutic agent and/or methods of the present invention can be administered to patients who require treatment of inflammation associated with any condition or disease, specifically, inflammatory bowel diseases (in particular, ulcerative colitis, Crohn's disease), psoriasis, atopic dermatitis, asthma, arteriosclerosis, tissue damage caused by ischemic reperfusion, acute respiratory distress syndrome, and so forth. The condition may also be or be associated with an auto-immune disease, nephritis, myocarditis, autoimmune hepatopathy, multiple sclerosis, rheumatism or other disorder. By way of example, the medical condition associated with inflammation may be selected from the group consisting of type 1 diabetes (e.g. diabetic nephropathy), rheumatoid arthritis, osteoarthritis, polyarthritis, gout, systemic lupus erythematosus, scleroderma, Sjorgen's syndrome, poly- and dermatomyositis, vasculitis, tendonitis, synovitis, bacterial endocarditis, osteomyelitis, psoriasis, pneumonia, fibrosing alveolitis, chronic bronchitis, chronic obstructive pulmonary disease (COPD), bronchiectasis, emphysema, silicosis, tuberculosis, ulcerative colitis and Crohn's disease.chronic inflammatory demyelinating polyradiculoneuropathy, chronic inflammatory demyelinating polyneuropathy, multiple sclerosis, Guillan-Barre Syndrome and myasthemia gravis, mastitis, laminitis, laryngitis, chronic cholecystitis, Hashimoto's thyroiditis, and including chronic inflammatory renal disease. In a further embodiment of the present invention said condition is an inflammatory renal disease, such as glomerulonephritis, crescentic glomerulonephritis, lupus nephritis, ANCA-associated glomerulonephritis, focal and segmental necrotizing glomerulonephritis, IgA nephropathy, membranoproliferative glomerulonephritis, cryoglobulinaemia and tubulointerstitial nephritis and tubulointerstitial nephritis. In a further embodiment of the present invention the medical condition associated with inflammation refers to prostate cancer, acute lymphoblastic leukemia, multiple myeloma, non-Hodgkin lymphoma or bladder cancer.

In the present invention "treatment" generally means to obtain a desired pharmacological effect and/or physiological effect. The effect may be prophylactic in view of completely or partially preventing a disease and/or a symptom, or may be therapeutic in view of partially or completely curing a disease and/or adverse effect of the disease. In the present specification, "treatment" includes arbitrary treatments of diseases in mammals, in particular, humans, for example, the following treatments (a) to (c): (a) Prevention of onset of a disease or symptom in a patient who may have a predisposition of the disease or symptom, but is not yet diagnosed to have the predisposition; (b) Inhibition of a symptom of a disease, that is, prevention of progression of the symptom; (c) Amelioration of a symptom of a disease, that is, induction of regression of the disease or symptom. Either therapeutic and/or prophylactic treatment may require administration of a "therapeutically relevant amount"/"effective amount" or "level" of an active component, which refers to an amount sufficient to induce or cause the above mentioned treatments (a) to (c) or any other amount sufficient to cause a physiological effect relevant for treating the disorder.

The term "pharmaceutical composition" refers to a combination of the agent as described herein with a pharmaceutically acceptable carrier. The phrase "pharmaceutically-acceptable" refers to molecular entities and compositions that do not produce a severe allergic or similar untoward reaction when administered to a human. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. A pharmaceutical composition of the present invention can include pharmaceutically acceptable salts of the components therein. The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions. Tablets contain the active ingredient in admixture with non-toxic pharmaceutically acceptable excipients which are suitable for the manufacture of tablets. The tablets may be uncoated or they may be coated by known techniques to delay disintegration and absorption in the gastrointestinal tract and thereby provide a sustained action over a longer period.

Dosage levels of the order of from about 0.01 mg to about 500 mg per kilogram of body weight per day are useful in the treatment of the above-indicated conditions. For example, inflammation or GIO may be effectively treated by the administration of from about 0.01 to 50 mg of the compound per kilogram of body weight per day (about 0.5 mg to about 3.5 g per patient per day). The amount of active ingredient that may be combined with the carrier materials to produce a Single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. The invention relates also to a process or a method for the treatment of the above mentioned pathological conditions. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical compositions.

EXAMPLES

The following examples have been carried out in various mouse models as an example for the mammalian system. The invention is therefore applicable to all mammals, especially humans.

Figure 8:
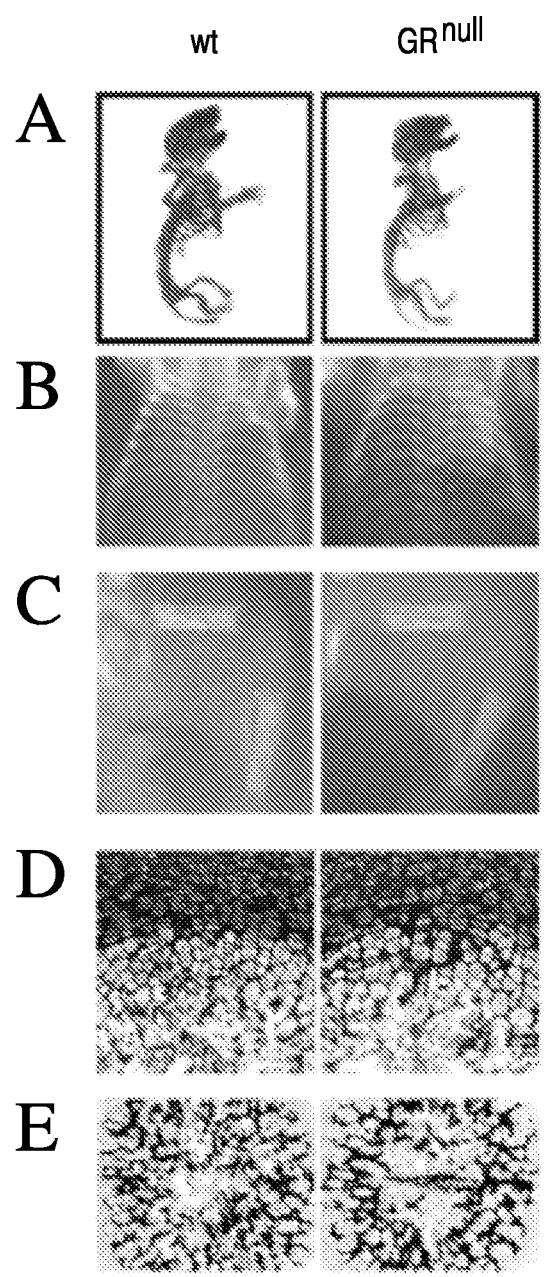
FIG. 8. Normal bone development in GR knockout mice. GR wild type (wt, left column) and GR knockout ($GR^{null}$, right column) embryos from the same litter were analyzed at stage 18.5 dpc. (A) Alcian Blue/Alizarin red staining of wt and $GR^{null}$ fetuses. (B, C) X-ray analysis of wt and $GR^{null}$ fetuses showing the rib cage (B) femur and tibia (C). (D) Sections through the growth plates of vertebrae of wt and $GR^{null}$ fetuses stained with toluidine blue. (E) Von Kossa staining of undecalcified sections from vertebral bodies.

Endogenous Glucocorticoid Action in Osteoblasts Increases Bone Mass but not Skeletal Development We initially asked whether endogenous GCs influence the development of the skeleton by using GR knockout ($GR^{null}$) mice. Alizarin Red/Alcian Blue staining did not reveal any differences in cartilage and calcified tissues in GR knockout ($GR^{null}$) compared to wild type E18.5 fetuses, and X-ray analysis showed similar bone mineral densities (FIG. 8A,B). The lack of gross alterations in growth plate dimensions and a similar extent of calcified bone revealed by von Kossa staining indicated that the development of skeletal tissues in $GR^{null}$ fetuses is normal (FIG. 8C,D).

Figure 9:
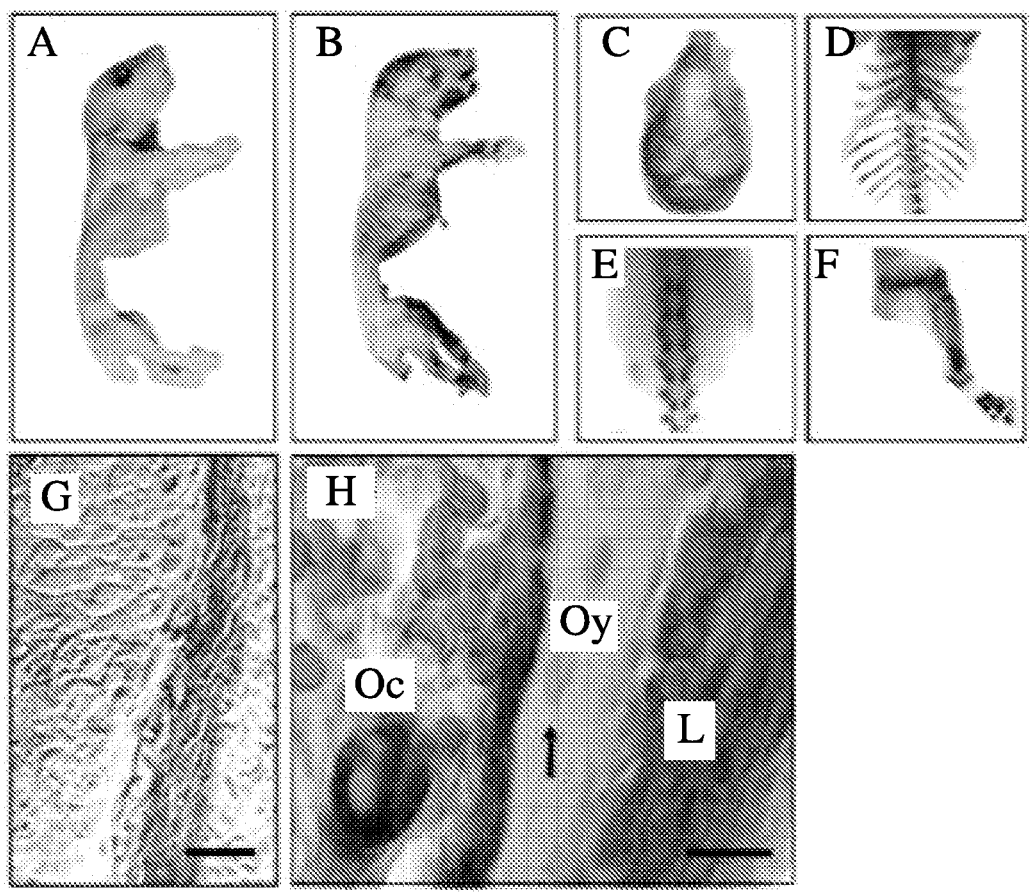
FIG. 9. Targeting the GR gene in the osteoblastic lineage. LacZ expression following Cre recombination was determined by whole mount staining in R26R/+heterozygous (A) and R26R/+x Runx2Cre (B-H) neonatal mice. Higher magnification shows lacZ expression in cells of the calvarial bone (C), rib cage (D), vertebrae, (E), and hind leg (F). (G) Section through the metatarsal growth plate shows lacZ expression in the growth plate and bone collar. Scale bar: 30 µm. (H) Section subjected to TRAP and X-gal staining reveals lacZ positive lining cells (L) and lacZ positive osteocytes (arrows), but lacZ negative TRAP-positive osteoclasts (asterisks). Scale bar: 15 µm. (I) Southern blot analysis of genomic DNA from indicated organs from $GR^{Runx2Cre}$ mice exhibits the non recombined GRflox fragment (upper band) and the Cre-induced recombined GRnull fragment (lower band). (J) PCR analysis of the non-recombined GRflox fragment (lower band) and the Cre-induced recombined $GR^{null}$ fragment (upper band) from embryonic cartilage and embryonic bone (both stage 15.5 dpc) and a heterozygous GRflox/null mouse as a control for the distribution of both alleles. Note that in cartilage there is less recombination in contrast to embryonic bone.
Figure 9:
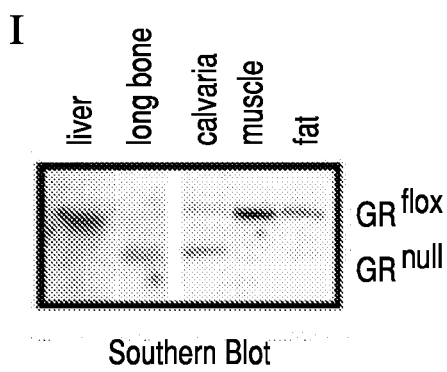
Figure 9:
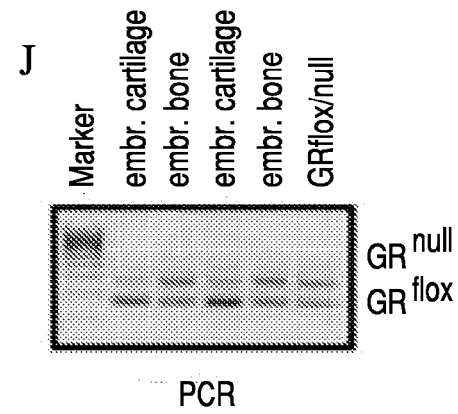

To allow investigations of GC actions in adult bone we disrupted the GR gene specifically in the osteoblast lineage by crossing $GR^{flox}$ mice (Tronche et al., 1999) with a novel osteoblast-specific Cre-transgenic mouse line (Runx2Cre) thereby obtaining $GR^{Runx2Cre}$ mice. Notably, efficient recombination at all sites of endochondral and intramembranous bone formation, particularly in periosteal cells, osteoblasts and osteocytes, but not in osteoclasts was observed when Runx2cre mice were crossed to a Rosa26 reporter strain (FIG. 9). In accordance with all known sites of Runx2 expression, $GR^{Runx2Cre}$ displayed almost complete recombination of the GR-flox allele in long bones, to a large extent in calvaria and to a minor part in cartilage. Recombination was undetectable in other mesenchymal tissues, i.e. muscle or fat (FIG. 9G,I,J). Thus, the GR is efficiently deleted in the osteoblastic lineage in $GR^{Runx2Cre}$ mice. Compared to control animals, females lacking the GR in osteoblasts exhibited no growth defects. Male mice showed a small increase in rump but not in tibia length, indicating a potentially minor role of the GR in the growth of the spine in males (FIG. 15).

Figure 1:
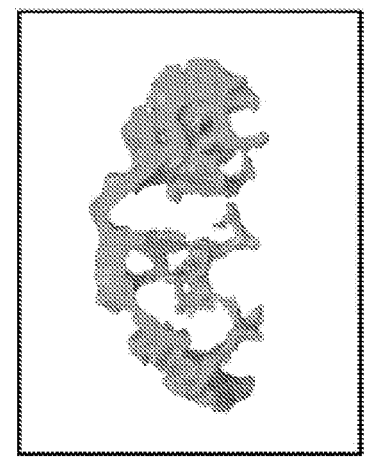
FIG. 1. Reduced bone mass in $GR^{Runx2Cre}$ mice (A) Micro-CT reconstruction of the trabecular part of vertebral L6 bodies of 10-week-old female $GR^{Runx2cre}$ and $GR^{flox}$ mice. (B) Histomorphometry of bone volume/tissue volume (BV/TV), trabecular thickness (TbTh), trabecular numbers (TbN), trabecular spacing (TbSp), (C) osteoblast number/bone perimeter (Ob.N/B.Pm), osteoblast surface/bone surface (Ob.S/BS), osteoclast number/bone perimeter (Oc.N/B.Pm) and osteoclast surface/bone surface (Oc.S/BS). (D) Primary osteoblasts derived from wild type (wt) and $GR^{null}$ mice were induced with osteogenic differentiation medium and differentiation was analyzed by ALP staining after 10 days and Alizarin Red after 20 days. (E) Osteoblast mRNA expression levels (arbitrary units normalized to actin) for Runx2, Col1a1 (10 days of differentiation) and Bglap2 (20 days) determined by qRT-PCR. Data represent mean±SEM; *p<0.05; **p<0.01 (n=8 in B,C; n=3 in E).
Figure 1:
Figure 1:
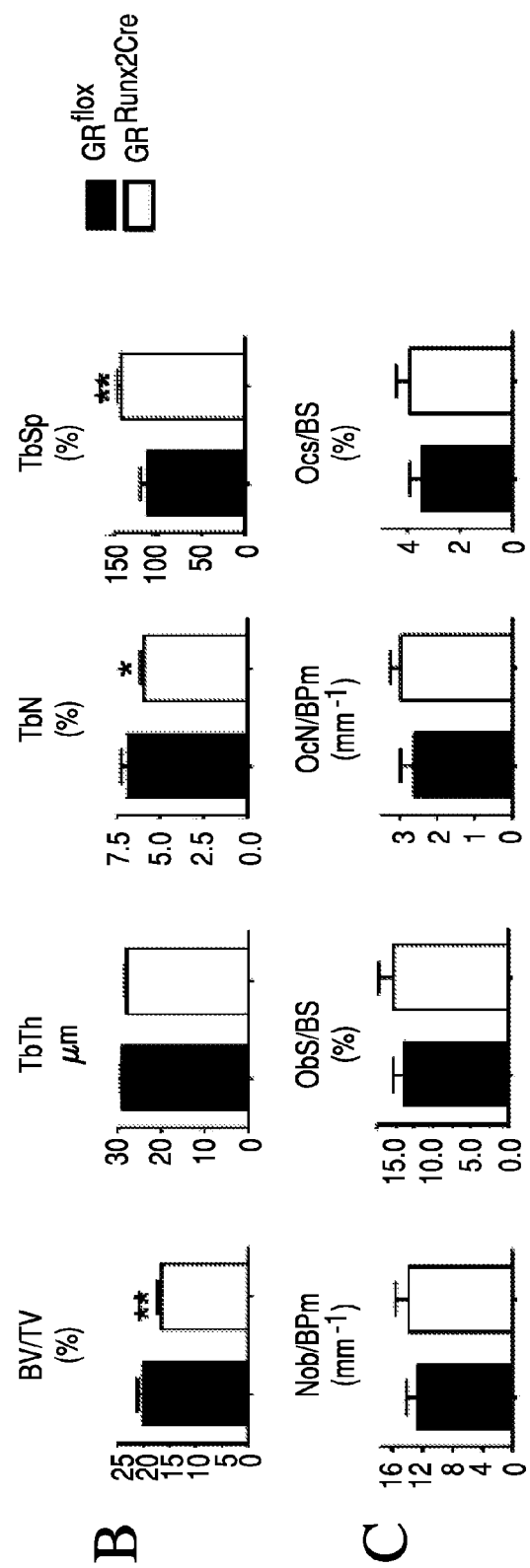
Figure 1:
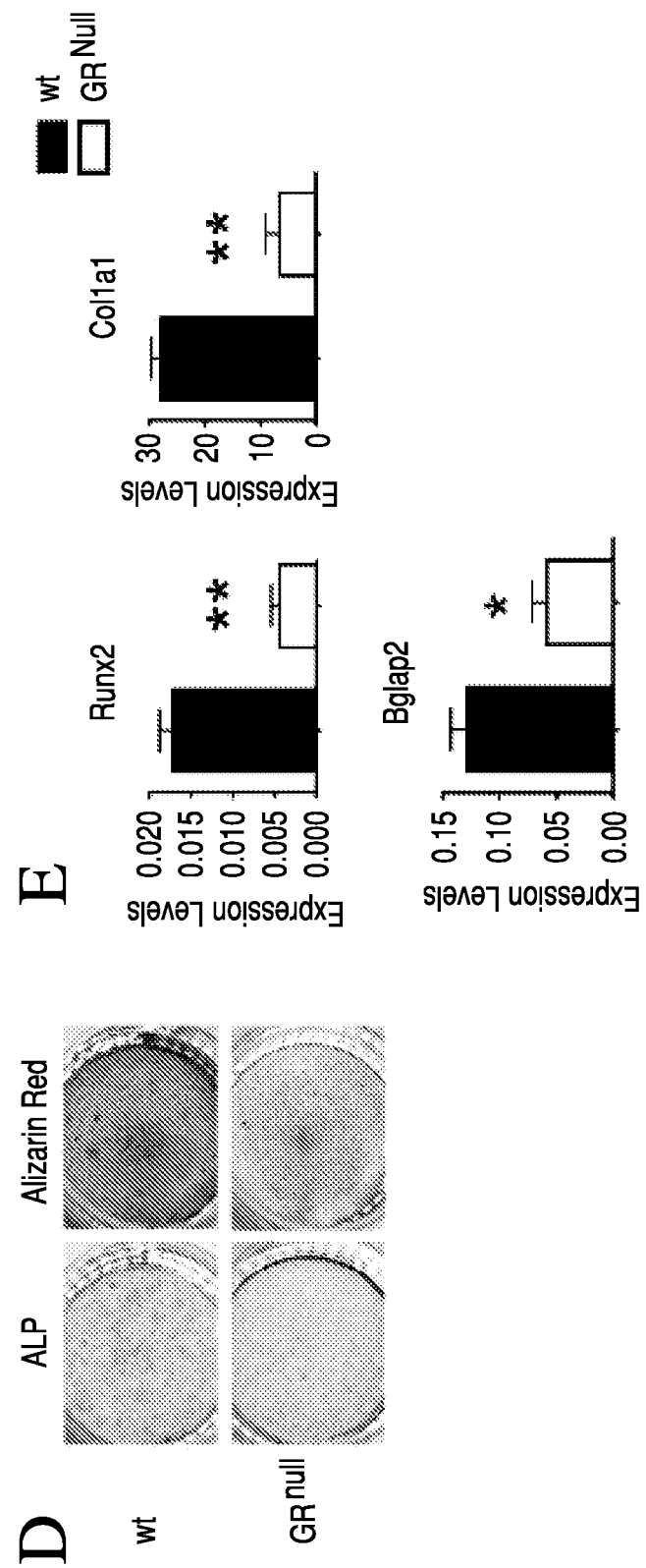

Micro-computer tomography (Micro-CT) analysis and bone histomorphometry of calcified vertebral sections of three-month-old female and male $GR^{Runx2Cre}$ mice revealed a modest, but highly significant, decrease of bone density compared to $GR^{flox}$ mice (FIG. 1A,B and data not shown). While trabecular thickness was not altered, the decrease was rather due to diminished trabecular numbers and consequently an increase in trabecular spacing (FIG. 1B). Numbers of osteoblasts, osteoblast surface, osteocytes and osteoclast parameters were not significantly changed (FIG. 1C). We therefore hypothesized that lack of the GR affects the differentiation towards functional osteoblasts, rather than their numbers per se. Indeed, as suggested by previous reports on mouse models deficient in GC action (Durbridge et al., 1990; Kaiak et al., 2009; Sher et al., 2006; Sher et al., 2004), calvarial osteoblasts from GR-deficient mice displayed a diminished differentiation potential in terms of alkaline phosphatase (ALP) expression and bone nodule formation (FIG. 1D). Accordingly expression of marker genes for osteoblast differentiation and function such as Runx2, Col1a1 and Bglap2 (osteocalcin) was reduced (FIG. 1E).

GR in Osteoblasts Mediates GC-Suppression of Bone Formation

Figure 2:
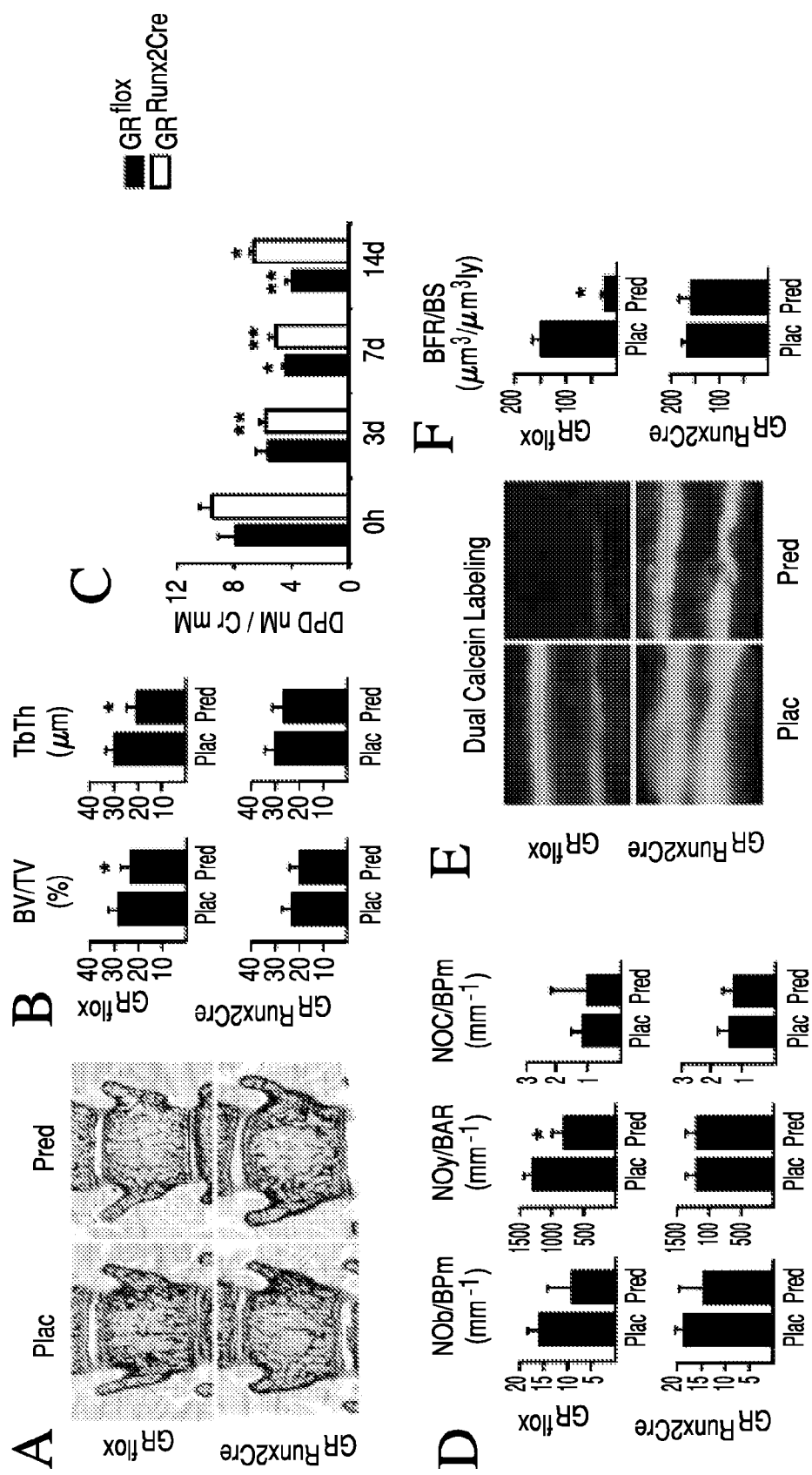
FIG. 2. Prednisolone reduces bone formation dependent on the GR in osteoblasts. Vertebral bodies of 10-week-old female $GR^{Runx2cre}$ and $GR^{flox}$ mice treated with placebo (Plac) or prednisolone (Pred; 12.5 mg/kg/day) for two weeks were analyzed by (A) von Kossa staining of undecalcified sections and (B) histomorphometry of BV/TV and TbTh. (C) DPD/Cr levels in urine of mice after prednisolone treatment at indicated times. (D) Histomorphometry of osteoblast number/bone perimeter (NOb/BPm), osteocyte number/bone area (NOy/BAR) and osteoclast number/bone perimeter (NOc/BPm). (E) Fluorescent micrographs of dual calcein labeling and (F) its quantitative analysis of bone formation rate/bone surface (BFR/BS). (G) Number of CFU-OBs within the bone marrow/leg (femur and tibia) and (H) qRT-PCR-determined Col1a1 mRNA expression in long bones of mice treated with placebo or prednisolone for three days. (I) Fluorescent micrographs of dual calcein labeling and (J) its quantitative analysis of BFR/BS in tibiae of $GR^{LysMcre}$ and corresponding $GR^{flox}$ control mice. Data represent mean±SEM; *p<0.05, **p<0.01 (n=5-6).
Figure 2:
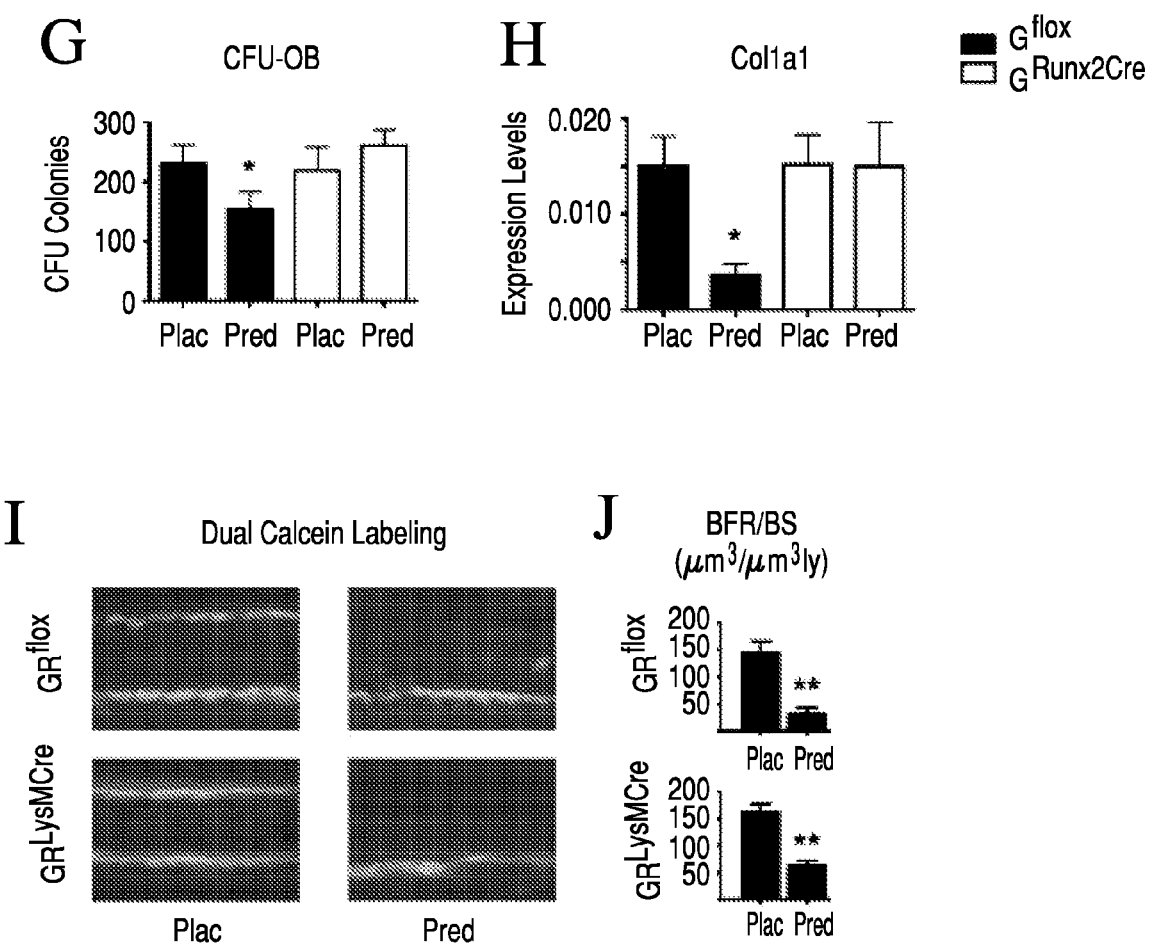

To address the role of the GR in osteoblasts in GC-induced bone loss, $GR^{Runx2Cre}$ and $GR^{flox}$ mice were treated with the clinically relevant GR agonist prednisolone for two weeks. As expected, prednisolone led to a reduced bone mineral density in vertebral bones of wild type mice due to decreased trabecular thickness. In contrast, these parameters were not affected in $GR^{Runx2Cre}$ mice (FIG. 2A,B). Resorption, as assessed by deoxypyridinoline (DPD/Cr) levels, was not increased by prednisolone but rather slightly decreased in mice of both genotypes (FIG. 2C); however, osteoclast numbers were not affected (FIG. 2D). In contrast, the numbers of osteocytes, osteoblasts (FIG. 2D) and the osteoblast surface (data not shown) were decreased in GR$^{flox}$ mice after prednisolone treatment, while the same parameters were unaltered in GR$^{Runx2Cre}$ mice.

Figure 10:
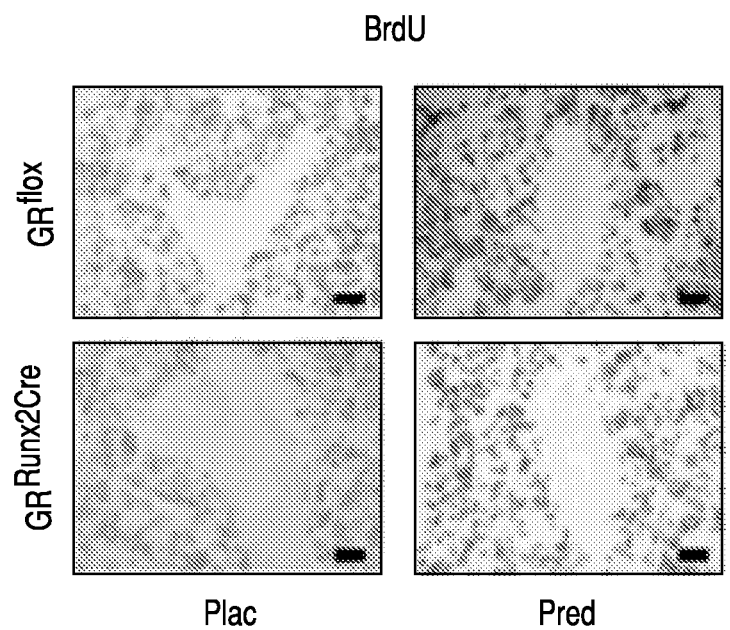
FIG. 10. Proliferation and apoptosis in bones of prednisolone treated $GR^{Runx2Cre}$ animals. (A, B). $GR^{flox}$ and $GR^{Runx2Cre}$ mice were treated with prednisolone for one day pulsed with BrdU for 4 hours and histological sections of long bones stained with anti-BrdU antibody (A) and with a TUNEL kit (B). BM: bone marrow; Scale bar: 20 µm.
Figure 10:
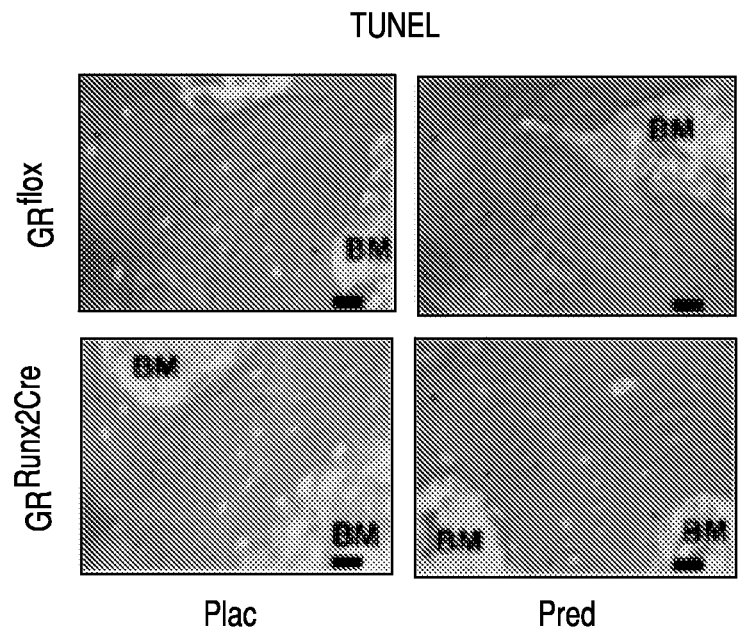

Most importantly, while prednisolone caused an almost complete inhibition of bone formation as determined by dynamic histomorphometry following dual calcein labeling in vertebrae of wild type mice, GR$^{Runx2cre}$ mice were fully protected (FIG. 2E,F). Since resorption was only slightly altered after prednisolone treatment, this complete block of bone formation is presumably the major cause for prednisolone-induced bone loss in wild type mice. Notably, prednisolone did not alter TUNEL and BrdU pulse labeling directly within bone tissue (FIG. 10). But osteoblastogenesis, in terms of colony forming units of osteoblasts (CFU-OBs), was strongly impaired in GR$^{flox}$ mice but not in GR$^{Runx2Cre}$ mice after three days of prednisolone treatment (FIG. 2G). Most strikingly, the expression of the marker for functional osteoblasts, Col1a1, was strongly reduced after three days of prednisolone in GR$^{flox}$ mice, whereas it remained unchanged in GR$^{Runx2Cre}$ mice (FIG. 2H), indicating suppression of osteoblast differentiation and function via the GR in these cells.

GCs Inhibit Bone Formation Via the GR in Osteoblasts

The data demonstrates that the GR in osteoblasts is essential for GIO, since prednisolone failed to reduce the bone formation rate, bone mass and trabecular thickness in GR$^{Runx2Cre}$ mice. Additionally, GC-mediated suppression of Col1a1 required the presence of the GR in osteoblasts. The requirement of the GR also clearly shows that the prednisolone dose used here, which was established to be effective in mice with the FVB/N background strain, displays no unspecific toxic effects. Osteoclast numbers were hardly affected by prednisolone, while osteoblast and osteocyte counts were diminished in wild type but not in GR$^{Runx2Cre}$ mice. In contrast to other studies which detected a marginal increase (Weinstein et al., 1998), we did not detect additional apoptosis of osteoblasts and osteocytes by prednisolone treatment in vivo. This discrepancy may be due to different mouse strains. Thus, apoptosis of mature osteoblasts would not explain the strong decrease in osteoblast numbers. This effect rather becomes effective at the osteoblast progenitor level, since CFU-OBs were already reduced in wild type animals after three days of treatment. The observed reduction of osteocytes about 20-35% in combination with no observable changes in empty lacunae (data not shown) also argues against an enhanced apoptosis, and can be only explained by an absence bone formation allowing to remove osteocyte containing bone by still ongoing bone resorption.

In contrast to GR$^{Runx2Cre}$ mice, we found a similar reduction of bone mass, trabecular thickness, bone formation, osteoblast numbers and CFU-OBs by GCs in wild type and GR$^{dim}$ mice. These results clearly show that the GR in osteoblasts, but not its dimerization function, is required for inhibition of bone formation and consequently bone loss.

The GR in Myeloid Cells does not Affect Bone Formation

To test whether the GR in osteoclasts influences bone formation during GC treatment, GR$^{LysMCre}$ mice lacking the GR in myeloid cells, such as monocytes, macrophages, neutrophils and osteoclasts (Tuckermann et al., 2007; unpublished observations), were treated with prednisolone for two weeks. The bone formation rate was similarly reduced in GR$^{LysMCre}$ and wild type mice (FIG. 2I,J), thus excluding a role for these cells in mediating GC-induced bone loss.

GC-Induced Bone Loss Occurs in the Absence of GR Dimerization

Figure 3:
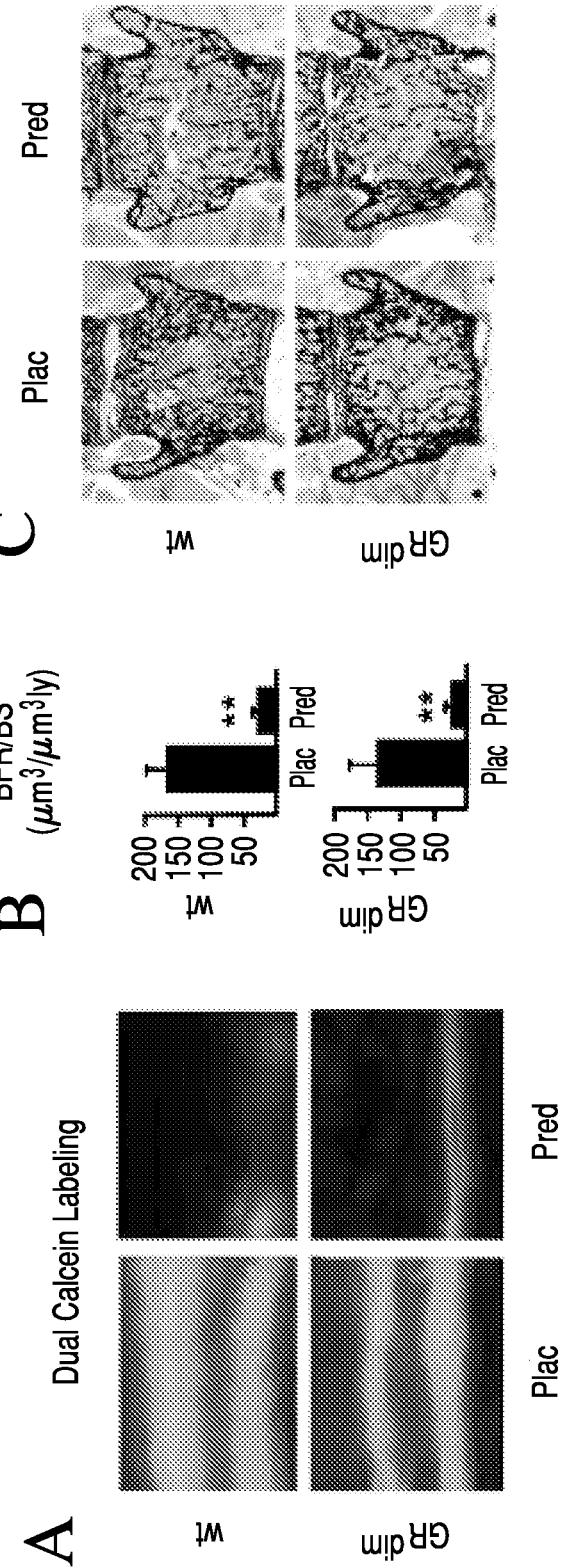
FIG. 3. $GR^{dim}$ mice respond to prednisolone with suppression of bone formation. (A) Fluorescent micrographs of dual calcein labeling and (B) its quantitative analysis of BFR/BS in vertebrae of $GR^{dim}$ and wild type (wt) mice treated as described in FIG. 2. (C) Vertebral bodies were analyzed by von Kossa staining of undecalcified sections. (D) Histomorphometry of BV/TV, TbTh, (E) NOb/BPm, NOy/BAR and NOc/BPm. (F) Number of CFU-OBs within the bone marrow/leg and (G) qRT-PCR-determined Col1a1 mRNA expression in long bones of mice treated with placebo or prednisolone for three days. (H) DPD/Cr levels in urine of mice after prednisolone treatment at indicated times. Data represent mean±SEM; *p<0.05, **p<0.01 (n=5-6).
Figure 3:
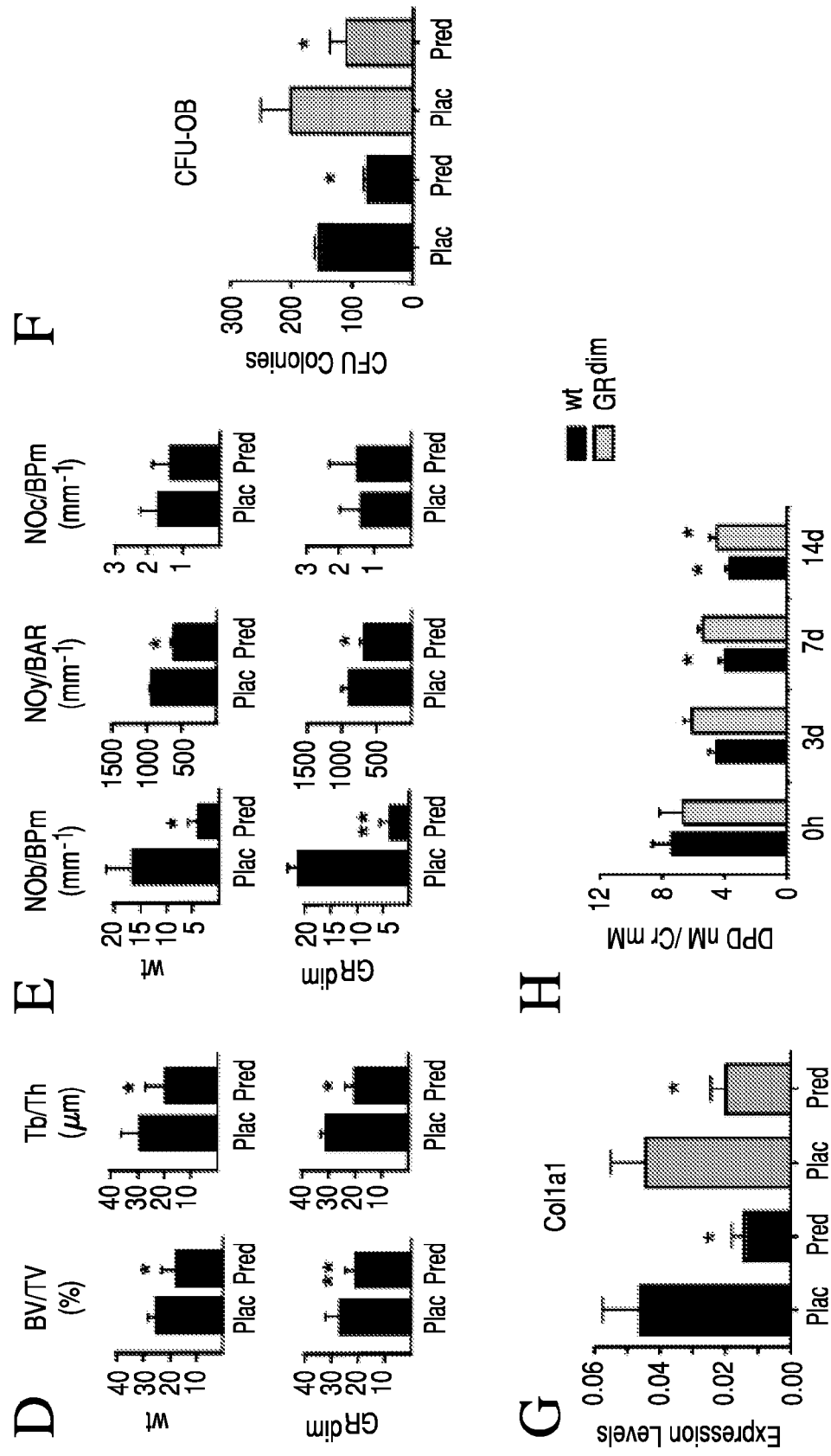

Although it had been hypothesized that GR dimerization was essential for many side effects of GC therapy, its role in bone loss has not been previously investigated. Therefore, GR$^{dim}$ mice carrying a dimerization-defective GR were treated with prednisolone. In contrast to GR$^{Runx2Cre}$ mice, bone formation was similarly repressed in GR$^{dim}$ and wild type mice, and bone mass and trabecular thickness of the vertebrae were reduced to a comparable degree (FIG. 3A-D). This was again accompanied by a strong reduction of osteoblast and osteocyte numbers (FIG. 3E), as well as osteoblast surface (data not shown) in both genotypes. Osteoblastogenesis in vitro was as efficiently suppressed in GR$^{dim}$ as in wild type mice, and Col1a1 expression was similarly reduced in both genotypes (FIG. 3F,G). Whereas osteoclast numbers were not changed, resorption was slightly decreased in both mouse strains (FIG. 3E,H).

Figure 4:
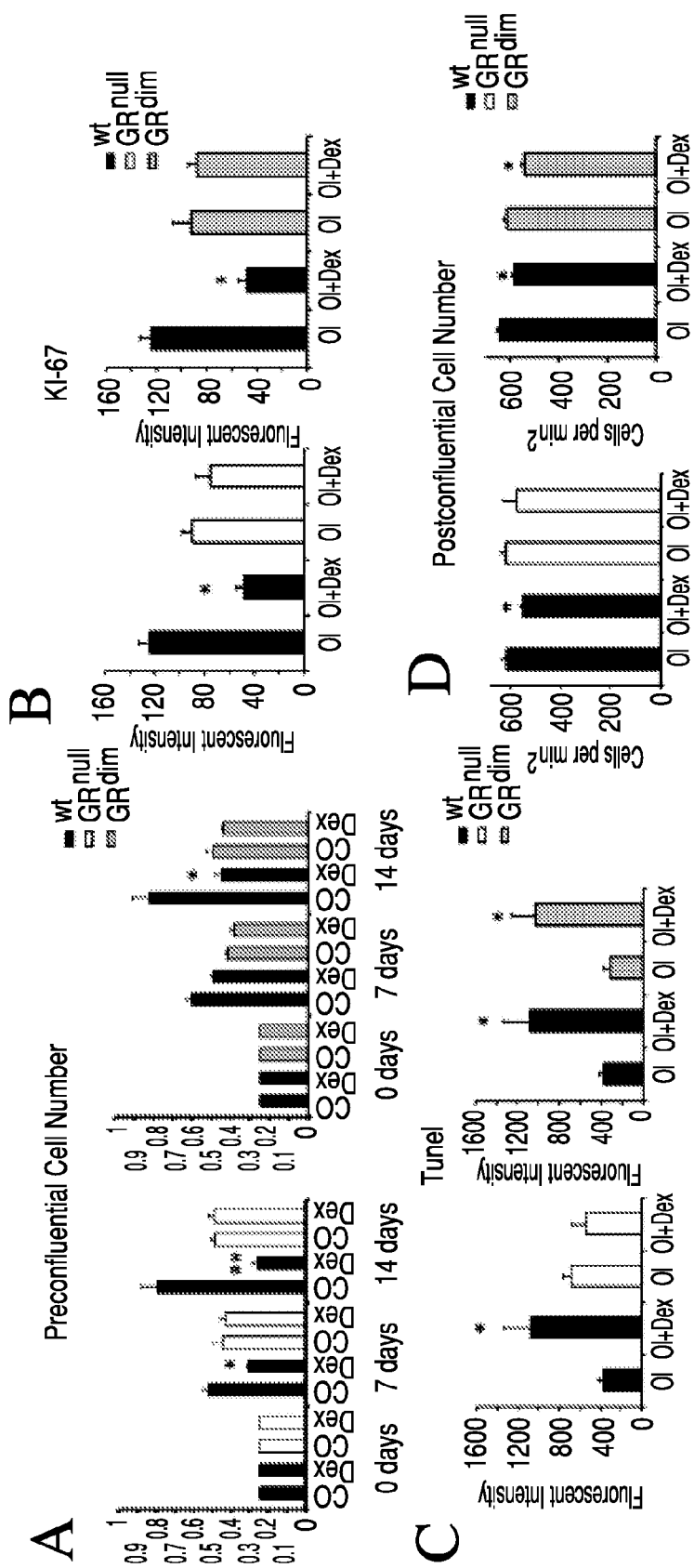
FIG. 4. Dimerization of the GR is required for inhibition of osteoblast proliferation, but not for induction of apoptosis and suppression of differentiation. (A) Primary mouse osteoblasts were treated without (Co) or with 1 µM Dex (Dex), and cell numbers were assessed at indicated days. (B-D) Primary osteoblasts were grown until confluence and were induced with osteogenic differentiation medium (OI) or in addition treated with 1 µM Dex (OI+Dex). At day 3, (B) Ki-67 content and (C) TUNEL labeling were analyzed, while (D) cell numbers were counted at day 10 using automated microscopy. (E, F) Primary osteoblasts after osteogenic induction, with or without Dex, were stained for ALP activity and calcification with Alizarin Red at indicated days. (G-J) qRT-PCR-determined osteoblast mRNA expression levels of Akp1(ALP), Runx2, Col1a1 (10 days of differentiation) and Bglap2 (20 days). Data represent mean±SEM; *p<0.05, **p<0.01 (n=3).
Figure 4:
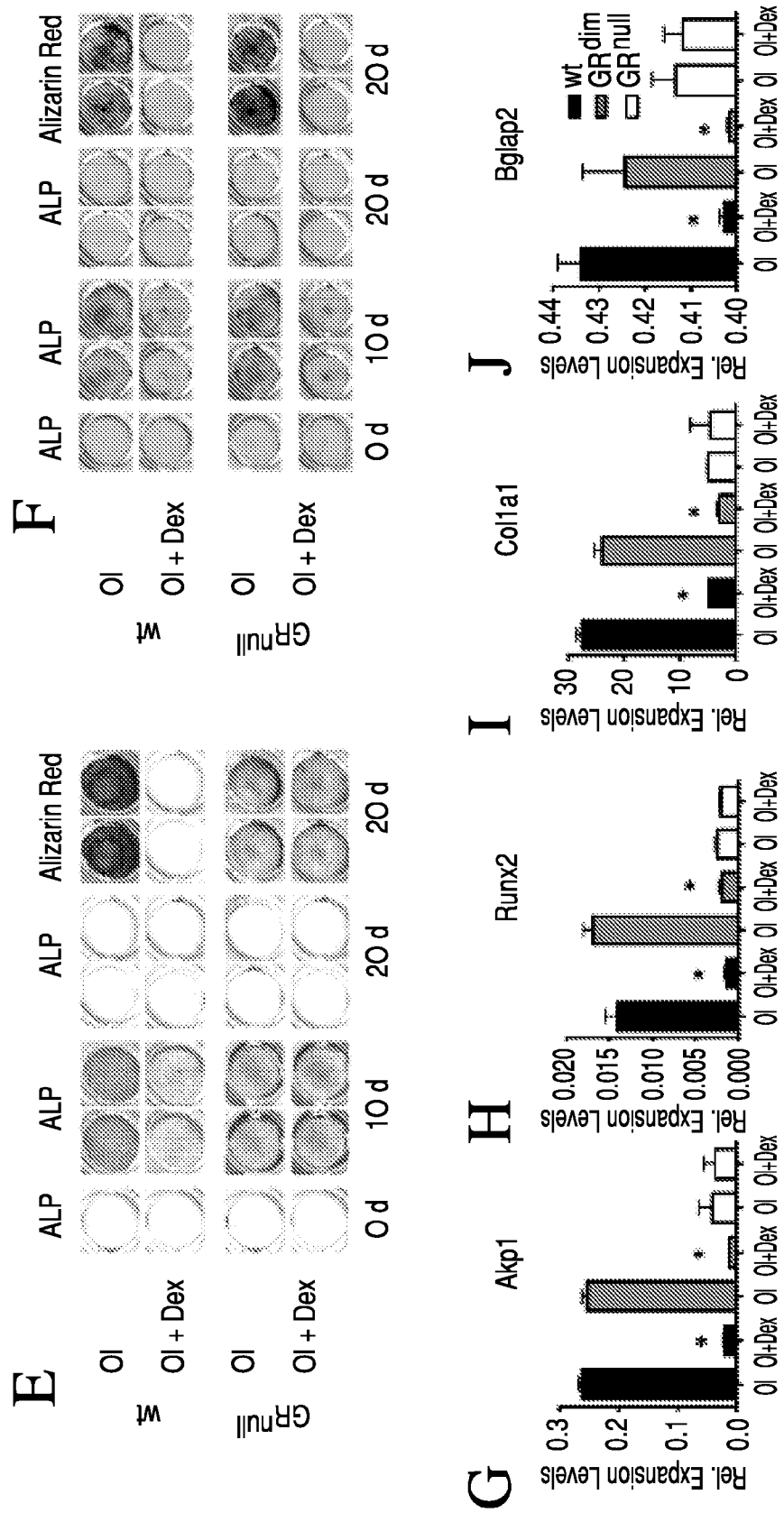

Dimerized GR Affects Osteoblast Proliferation but not Apoptosis and Differentiation Primary osteoblasts from wild type, GR$^{null}$ and GR$^{dim}$ mice were cultured in vitro to determine the contribution of GR dimerization to GC effects on osteoblasts. Proliferation of preconfluent pre-osteoblasts isolated from neonatal calvaria was lower in cultures of both GR$^{null}$ and GR$^{dim}$ cells as compared to wild type controls, suggesting that the GR promotes osteoblast expansion in the presence of basal GC concentrations (FIG. 4A). In contrast, treatment with dexamethasone (Dex) completely prevented expansion of wild type cells but did not affect GR$^{null}$ and GR$^{dim}$ cultures. Thus, GR dimerization is required for permissive and repressive GC activities on osteoblast expansion.

Figure 11:
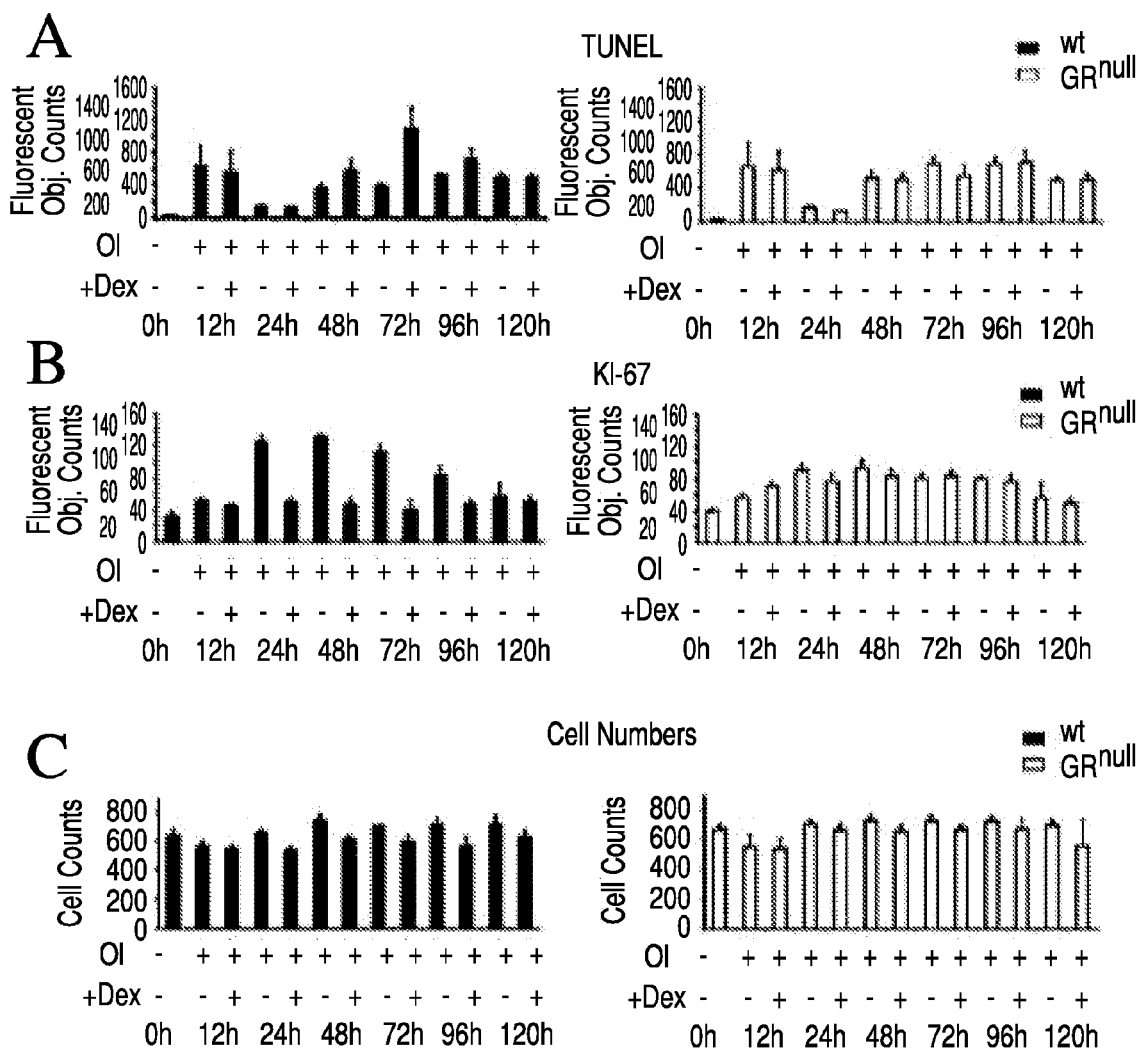
FIG. 11. Proliferation, apoptosis and osteoblast cell numbers are affected during the first 72 hours depending on the GR. Primary osteoblasts from the wt and $GR^{null}$ mentioned above were grown until confluence and subsequently induced with osteogenic differentiation medium (OI) or in addition treated with Dex (OI+Dex). At indicated time points TUNEL labeling (A) and Ki67 content (B) were analyzed while cell numbers were counted using automated microscopy (C).
Figure 12:
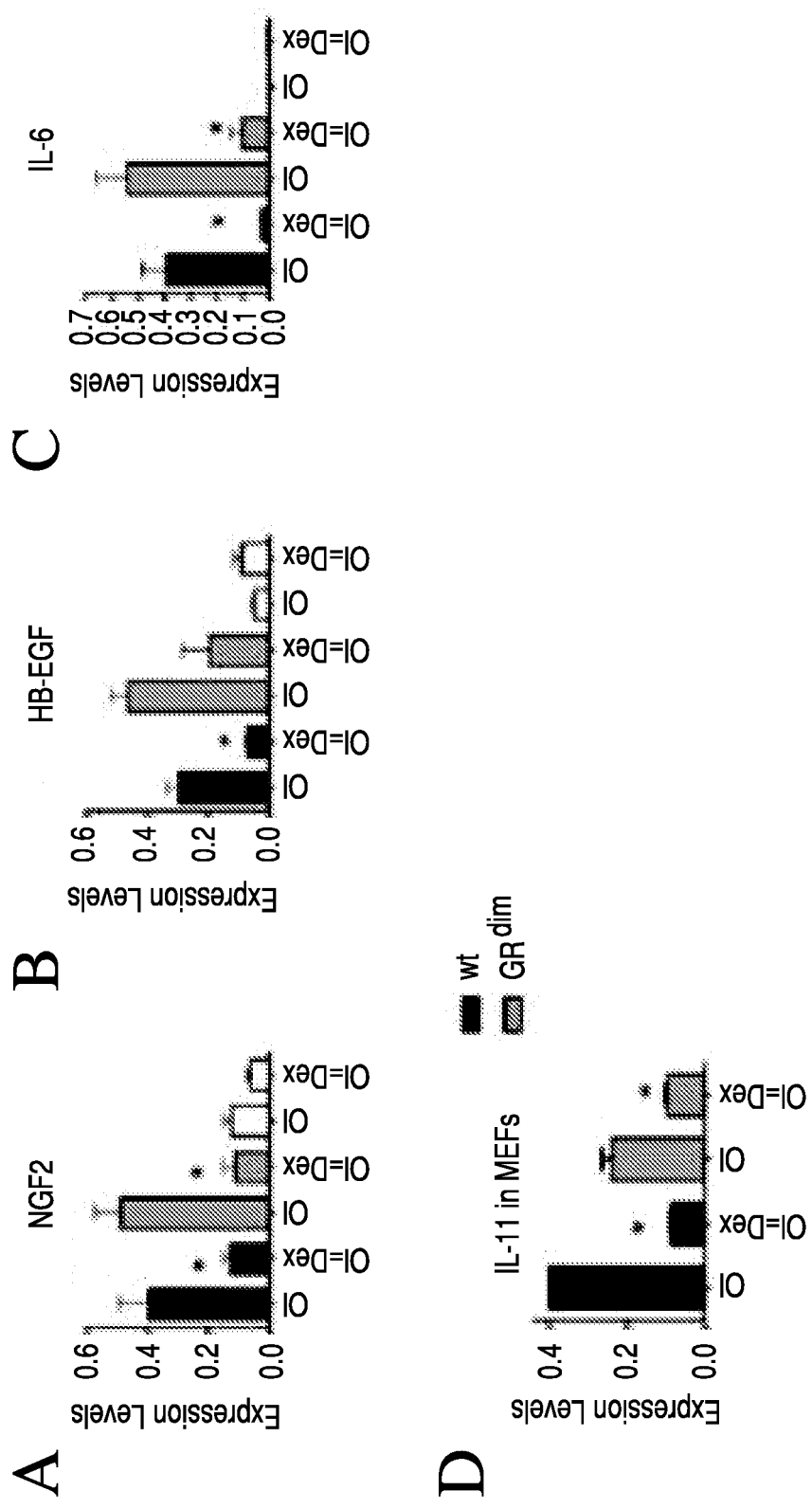
FIG. 12. Cytokines and growth factors are efficiently suppressed in $GR^{dim}$ osteoblasts and mouse embryonic fibroblasts. Primary osteoblasts (A-C) from wild type, $GR^{null}$ and $GR^{dim}$ animals were isolated and at confluency induced with osteogenic differentiation medium (OI) or in addition treated with Dex (OI+Dex). After 6 hours mRNA expression was determined by quantitative RT-PCR. mRNA expression levels are depicted as arbitrary units normalized to actin mRNA expression for NGFb (NGF2) (A), Hbegf (HB-EGF) (B) and Il6 (IL-6) (C). (D) Mouse embryonic fibroblasts (MEFs) were treated as above and mRNA levels for Il11 (IL-11) were determined by quantitative real time PCR. Data are represented as mean+/−SEM. *<0.05.

Postconfluential proliferation after exposure to osteogenic conditions has been reported to accompany osteoblastic differentiation in vitro (Smith et al., 2000). Ki-67-stained wild type cells confirmed reduction of proliferation by Dex after 24 hours until 96 hours (FIG. 11B). In contrast, postconfluential proliferation of GR$^{dim}$ and GR$^{null}$ cells was entirely unaffected by Dex (FIG. 4B). Additionally, Dex-induced apoptosis was observed in wild type and GR$^{dim}$ cells but not in GR$^{null}$ cells (FIG. 4C, 11A). This is consistent with the slight reduction in postconfluential cell numbers by Dex in wild type and GR$^{dim}$ but not in GR$^{null}$ cells (FIG. 4D, 11C). ALP activity and matrix mineralization were inhibited by Dex treatment of wild type and GR$^{dim}$ but not of GR$^{null}$ osteoblasts (FIG. 4E,F). Efficient down-regulation of the osteoblastic markers Runx2, Akp1, Col1a1 and Bglap2 confirmed inhibition of osteoblast differentiation of wild type and GR$^{dim}$ cells. In contrast, no repressive effect of Dex was observed for GR$^{null}$ osteoblasts (FIG. 4G-J).

Inhibition of Bone Formation and Osteoblastogenesis is Independent of GR Dimerization We have described for the first time complete suppression of osteoblast differentiation in vitro and GC-induced bone loss in vivo in the absence of GR-DNA binding. Osteoblast differentiation in GR$^{dim}$ calvarial osteoblasts was as efficiently inhibited by GCs as in wild type cells; however, only a low level of apoptosis was induced by GCs in wild type and GR$^{dim}$ osteoblasts in vitro. More strikingly, neither we failed to detect enhanced apoptosis in vivo at several time points, nor did we detect a change of empty lacunae, an indication of apoptotic loss of osteocytes (data not shown). These findings argue against an important role of cell death in GIO, as previously proposed (Weinstein et al., 1998).

Proliferation of GR$^{dim}$ osteoblasts could not be inhibited by GCs either before or after confluence. In view of the previously reported role of proliferation for subsequent osteoblastic differentiation of MC-3T3 cells (Smith et al., 2000), the uncoupling of proliferation and differentiation in GR$^{dim}$ osteoblasts is surprising. Since osteoblast numbers, osteoblastogenesis, Col1a1 expression and bone formation were reduced by GCs in GR$^{dim}$ mice, we propose that inhibition of osteoblastogenesis, rather than inhibition of cell proliferation accounts for these effects.

The Monomeric GR in Osteoblasts and Osteoclasts Affects Osteoclastogenesis

Figure 5:
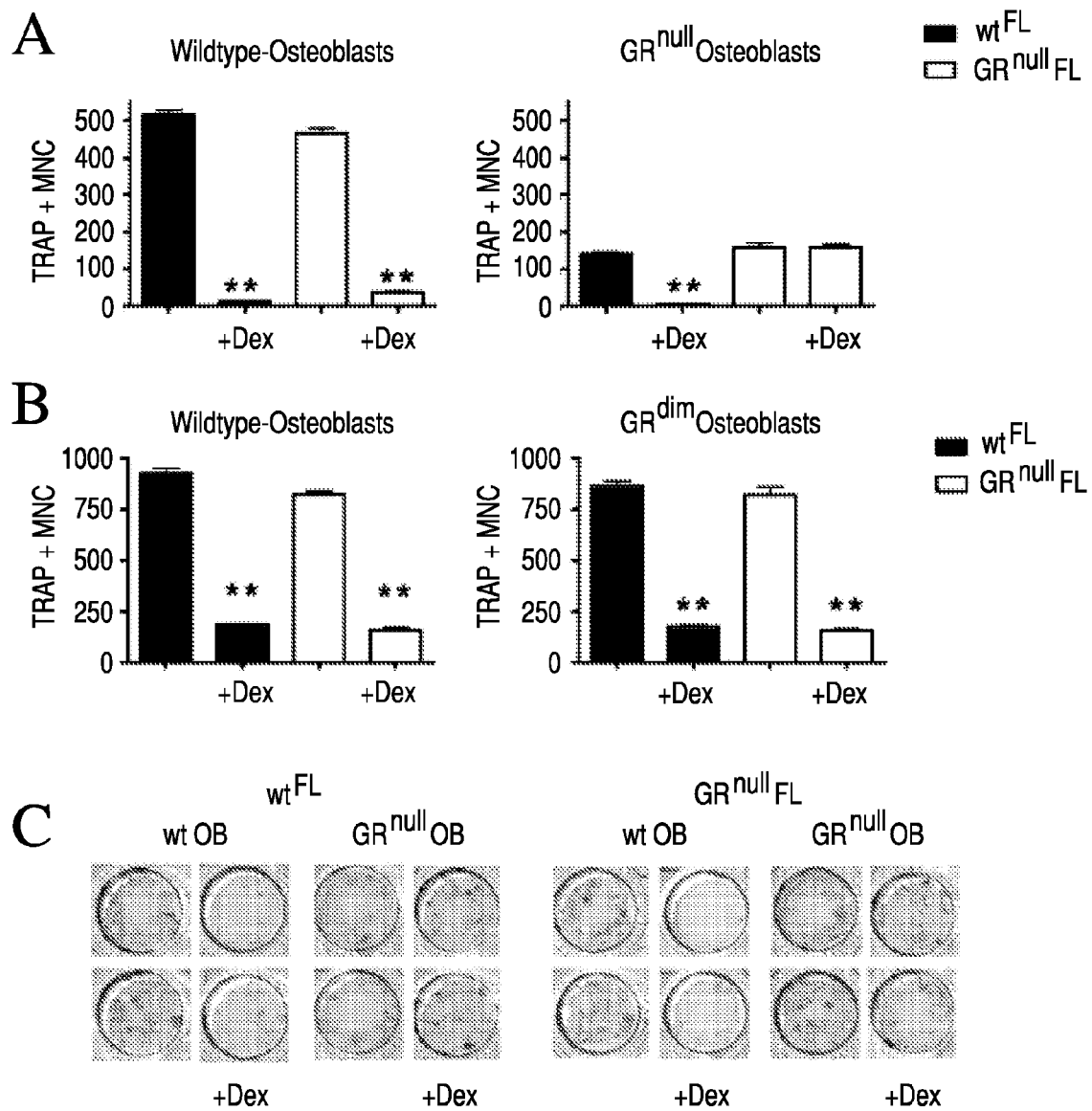
FIG. 5. Osteoclastogenesis is suppressed by GCs by the GR in osteoblasts and osteoclasts, independent of GR dimerization, whereas osteoblastogenesis depends solely on the osteoblast GR. (A) Wild type and $GR^{null}$ osteoblasts, and (B) wild type and $GR^{dim}$ osteoblasts were cultured with fetal liver cells (FL) derived from wild type or $GR^{null}$ mice in the presence of vitamin D3, with or without Dex. After seven days of culture, wells were stained with TRAP and TRAP MNCs were counted. (C) Wild type and $GR^{null}$ osteoblasts (OB) were cultured with fetal liver cells derived from wild type or $GR^{null}$ mice as in (A). ALP staining was performed after 10 days of co-culture under osteogenic conditions with or without Dex. (D) Wild type- and $GR^{dim}$-derived bone marrow-derived macrophages (BMDMs) were cultured with M-CSF (50 ng/ml) and RANKL (30 ng/ml) in the absence or presence of Dex. TRAP MNCs were determined after five days. (E, F) Wild type and $GR^{dim}$ BMDMs were cultured with M-CSF and RANKL in the presence or absence of Dex in osteological chambers coated with calcium phosphate to determine resorption area after five days of culture. Data represent mean±SEM; *p<0.05, **p<0.01 (n=4). Scale bar: 400 µm.
Figure 5:
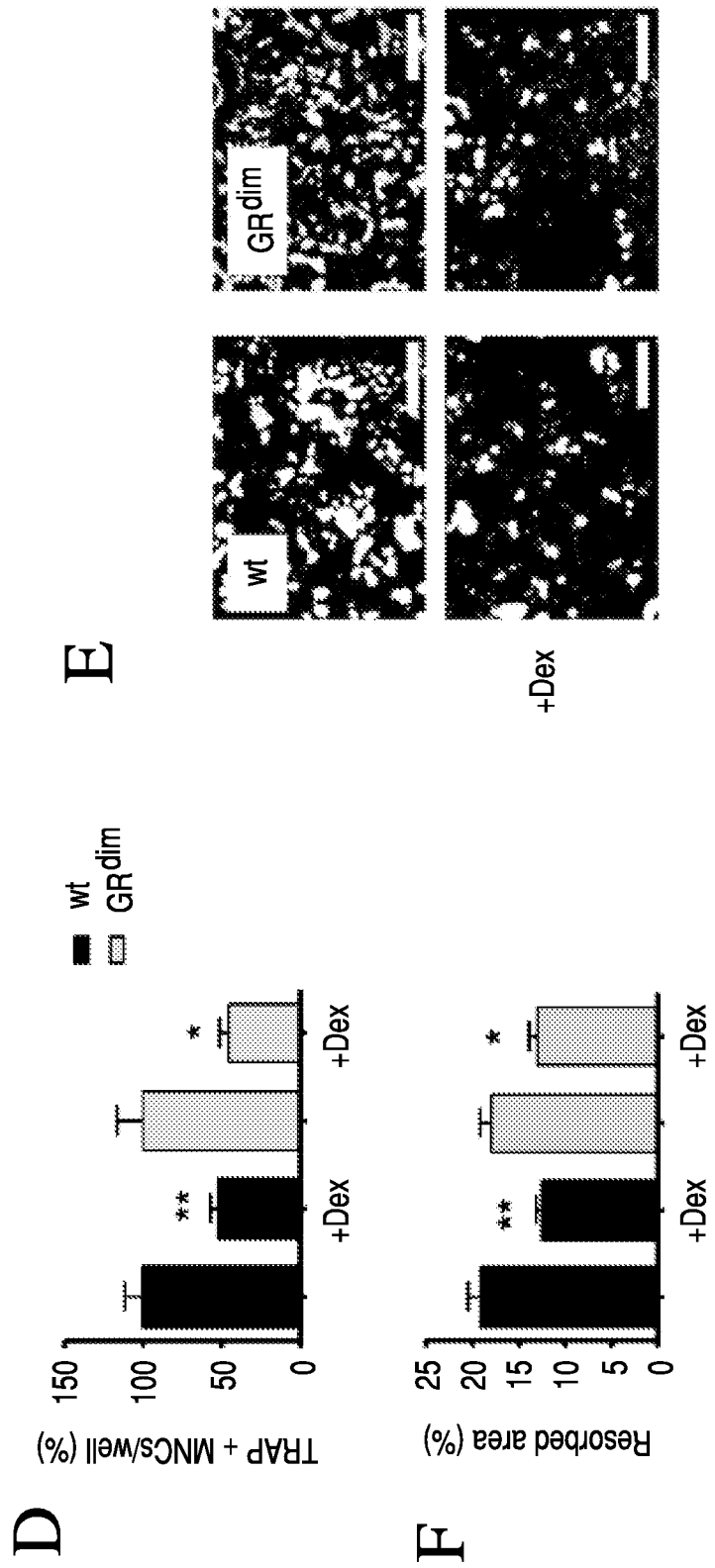

Since osteoblasts can stimulate the formation of osteoclasts, co-cultures of osteoblasts with wild type, GR$^{null}$ and GR$^{dim}$ fetal liver cells serving as osteoclast progenitors were established. Irrespective of whether the GR was present in osteoclasts, co-cultures with GR$^{null}$ osteoblasts under basal conditions led to the generation of fewer tartrate resistant alkaline phosphatase-positive multinuclear cells (TRAP MNCs) as compared to wild type osteoblasts (FIG. 5A). This indicates that the GR in osteoblasts contributes to osteoclastogenesis under low-dose GC conditions. A pharmacological dose of Dex reduced the number of TRAP MNCs in co-cultures independent of GR expression in the osteoclasts (FIG. 5A), again highlighting a major contribution of the GR in osteoblasts. Interestingly, Dex also repressed osteoclastogenesis when we co-cultivated GR$^{null}$ osteoblasts with wild type fetal liver cells, but not when the GR was absent from both cell compartments (FIG. 5A). Thus, the GR in both osteoblasts and osteoclasts mediates reduction of TRAP-positive cells by GCs.

Dimerization of the GR in osteoblasts was neither required for basal osteoclastogenesis nor for suppression of osteoclastogenesis by Dex (FIG. 5B). It is noteworthy that GR$^{dim}$ osteoclast differentiation from progenitor cells in the presence of M-CSF and RANKL was as efficiently prevented by Dex as in wild type controls in terms of TRAP MNCs capable of resorbing bone surfaces (FIG. 5D-F). Therefore, repression of osteoclastogenesis by GCs occurs independently of GR dimerization in both osteoblasts and osteoclasts. Suppression of osteoblast differentiation, however, is cell autonomous and is not influenced by the GR in osteoclasts. In co-cultures, ALP-positive osteoblasts were reduced only when the GR was present in osteoblasts, but were independent of its presence in osteoclasts (FIG. 5C).

The Role of the GR in Osteoclasts

Cell-autonomous effects of the GR in osteoclasts can lead to GC-enhanced bone resorption (Jia et al., 2006; Weinstein et al., 2002; Yao et al., 2008). We found a slightly decreased resorptive activity during the entire 14 days of GC treatment. Nevertheless, in the absence of de novo bone formation, the residual resorptive activity after prednisolone administration was apparently sufficient to lead to GC-induced bone loss in wild type and GR$^{dim}$ mice. This explains, why interfering with bone resorption using bisphosphonates (Weinstein et al., 2002) or inhibitory anti-RANKL antibodies (Hofbauer et al., 2009) ameliorates bone loss in GIO models.

In contrast to unaffected osteoclast numbers in vivo, pharmacological doses of GCs repressed osteoclastogenesis via the GR in osteoblasts and osteoclasts in vitro. The latter observation is in line with a report by Kim et al. (2006) showing that Dex inhibits osteoclast formation and spreading in vitro by a mechanism dependent on the GR in osteoclasts. The absence of changes of osteoclast numbers in vivo might be explained by a slow turnover of bone-residing osteoclasts, thus concealing the inhibitory effect observed in the co-culture experiments. Neither the direct inhibitory effects of GCs on isolated osteoclasts nor the indirect effects on osteoclastogenesis mediated by osteoblasts require GR dimerization.

Osteoclastogenesis proceeded normally in GR-deficient osteoclast progenitor cells. Likewise, we did not observe any differences in bone mass and trabecular thickness under physiological conditions in GR$^{LysMCre}$ mice lacking the GR in osteoclasts (data not shown). However, bone formation in GR$^{LysMCre}$ mice was similarly reduced upon GC treatment as in wild type animals. This is in striking contrast to a previous report using the same animal model (Kim et al., 2006), but in line with a study using TRAP-11b-HSD2 transgenic mice in the sense that GCs reduce osteoblast numbers and bone formation even when GC actions in osteoclasts cannot occur (Jia et al., 2006). However, an important role of the GR in osteoclasts for the increased bone resorption observed in humans and some mouse strains, such as Swiss Webster mice, cannot be excluded.

GCs Inhibit Osteoblastogenesis in the Absence of NF-KB Activity

Figure 6:
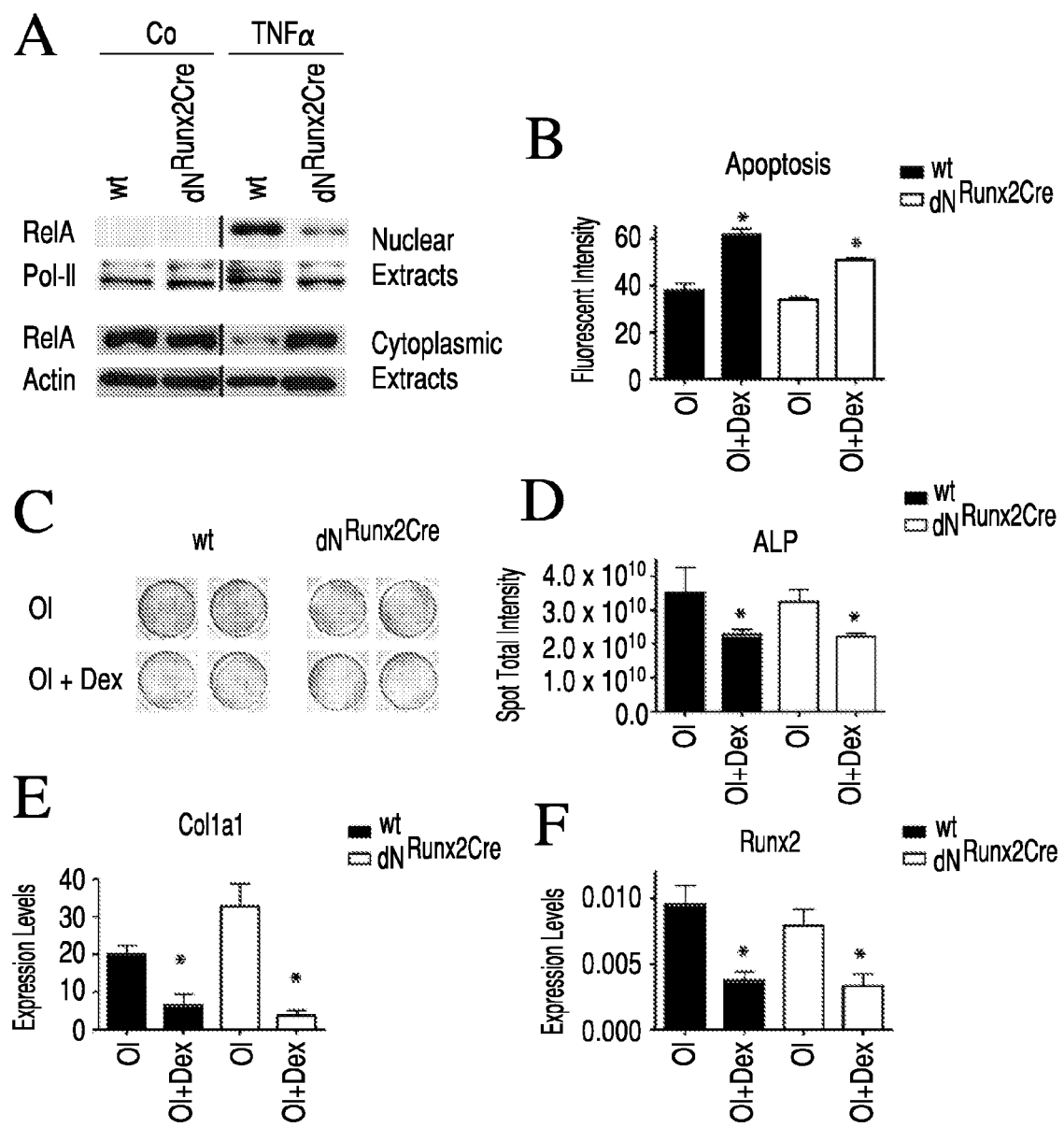
FIG. 6. Lack of NF-kB activity does not change the response of osteoblasts towards GCs. (A) Wild type and $dN^{Runx2Cre}$ osteoblasts were treated with TNF-alpha for 30 min. Nuclear and cytoplasmic extracts were analyzed by immunoblotting for p65, actin and polymerase II. (B, C) Primary osteoblasts were grown until confluence and treated as described in FIG. 4A. (B) TUNEL labeling was performed after three days. After 10 days ALP staining (C) and quantitative ALP activity (D) were examined. (E, F) qRT-PCR-determined osteoblast mRNA expression levels of Col1a1 and Runx2 (10 days of differentiation). Data represent mean±SEM; *p<0.05 (n=3).

The dimerization-defective receptor in GR$^{dim}$ mice is strongly impaired in direct DNA binding, but is still able to suppress osteoblast differentiation. Thus, a GR dimer-independent tethering mechanism with other transcription factors, such as NF-KB, could be crucial in this process. To test this hypothesis, we employed primary osteoblasts expressing a non-degradable N-terminal truncated IkBa (dN$^{Runx2Cre}$). By preventing its phosphorylation by IkB kinases this molecule acts as a dominant-suppressor of p65/p50 activation (Schmidt-Ullrich et al., 2001), whereas GR activity is not affected. Indeed, NF-KB activity was strongly reduced as indicated by the impaired nuclear translocation of NF-KB p65 after tumor necrosis factor (TNF)alpha treatment (FIG. 6A). Independent of diminished NF-KB activity, osteoblast apoptosis was normal after Dex treatment (FIG. 6B) and their differentiation was still efficiently inhibited by Dex based on reduced ALP activity and lower Col1a1 and Runx2 expression (FIG. 6C-F). Thus, it is unlikely that GCs inhibit bone formation via interference of the GR monomer with NF-KB activity.

Figure 7:
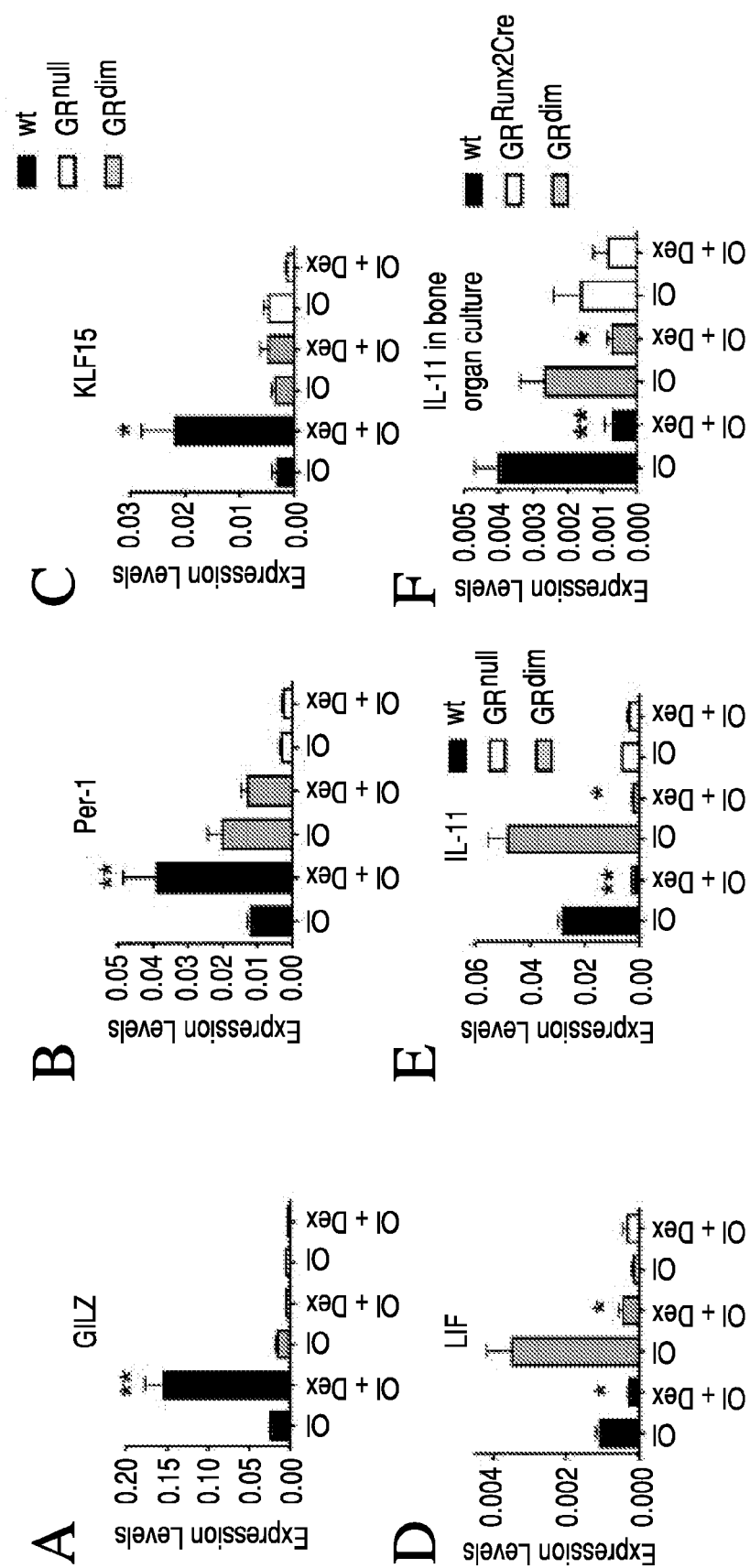
FIG. 7. Differential gene regulation in $GR^{dim}$ osteoblasts and bone organs by GCs and involvement of AP-1 in suppression of IL-11 in osteoblast differentiation. (A-E) Primary osteoblasts were grown until confluence and treated as described in FIG. 4A. qRT-PCR-determined mRNA expression levels of GILZ, Per-1, KLF15, Lif (LIF) and Il11 (IL-11) after six hours. (F-H) qRT-PCR-determined mRNA expression level of IL-11 in organ cultures of GR mutant fetal hind legs (F), in $dN^{Runx2Cre}$ osteoblasts (G) and c-jun$^{null}$ MEFs (H) after six hours treatment. (I) Chromatin immunoprecipitation of MEFs after six hours. Anti-GR precipitation revealed PCR amplified fragments of the IL-11 promoter encompassing functional AP-1 sites. IgG precipitation served as negative control and amplification of the input as positive control. (J) Primary wild type osteoblasts were differentiated with or without Dex and in the presence or absence of recombinant IL-11 10 ng/ml. At day 10, ALP activity was determined and at day 20, Alizarin Red staining was performed. (K) Quantification of ALP-positive cells treated as in (J) after 10 days. (L) qRT-PCR-determined Runx2 mRNA expression level in cells treated as in (J) after 10 days. Data represent mean±SEM; *p<0.05, **p<0.01 (n=3).
Figure 7:
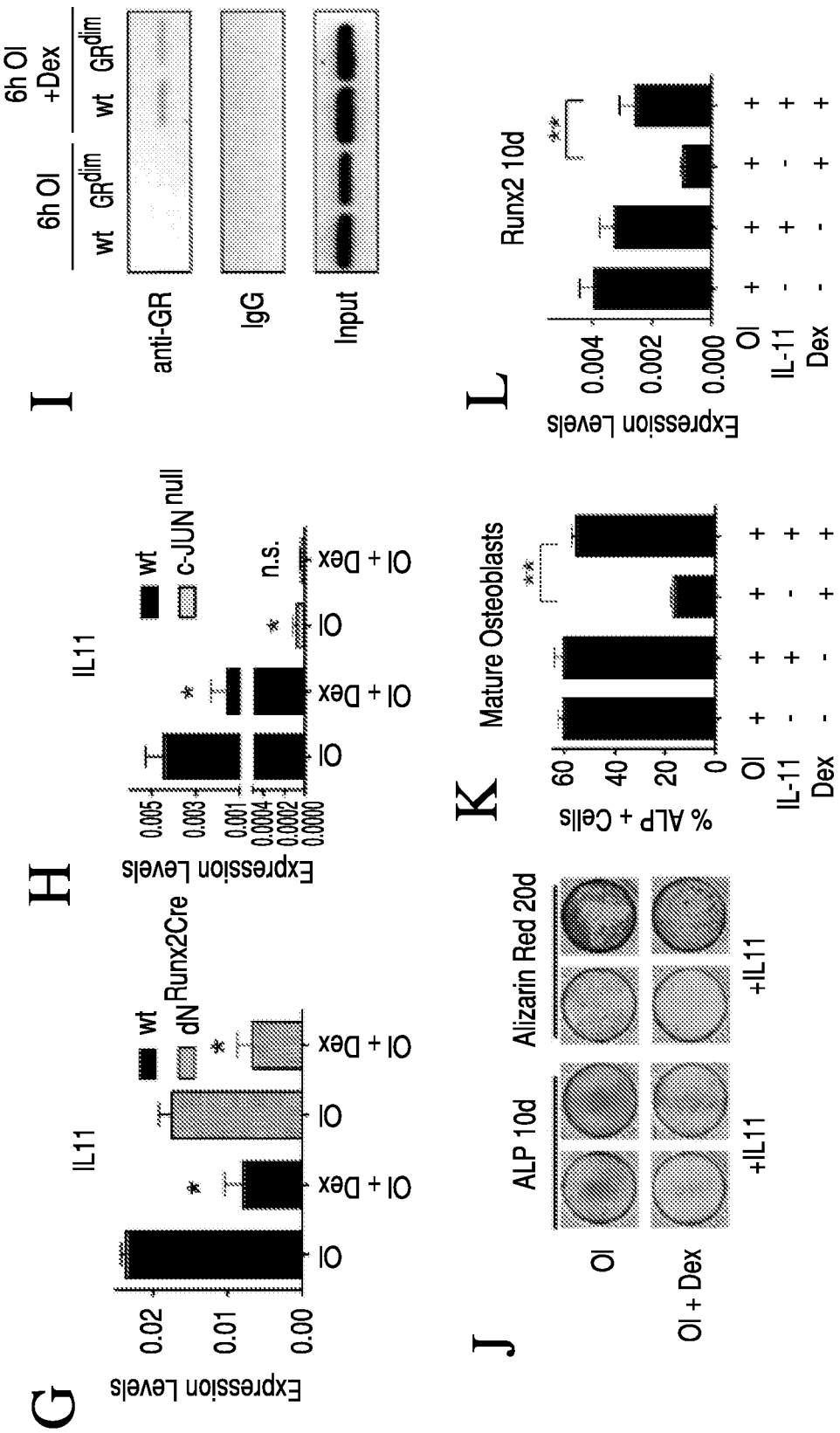

Tethering of GR to AP-1 Sites Inhibits IL-11 Expression Leading to Suppression of Osteoblast Differentiation To determine the molecular mechanism used by the monomeric GR to suppress osteoblast differentiation we performed quantitative PCR to identify genes potentially involved in this process. Firstly, we confirmed lack of induction of known GRE dependent genes by Dex in GR$^{dim}$ osteoblasts, namely the GC-induced leucine zipper (Tsc22d3, GILZ), the circadian rhythm gene Per-1 and the recently identified GR target gene KLF15 (Yoshikawa et al., 2009) in GR$^{dim}$ osteoblasts (FIG. 7A-C). In contrast, several growth factors and cytokines were similarly down regulated in both wild type and GR$^{dim}$ osteoblasts. Among them were the nerve growth factor 2 (NGF2), the heparin binding-epidermal growth factor (HB-EGF), IL-6, the leukemia inhibitory factor (LIF) and IL-11 that were down-regulated by GCs in both wild type and GR$^{dim}$ osteoblasts (FIG. 12A-C, 7D,E).

Since defective IL-11 signaling causes reduced bone formation in mice (Sims et al., 2005), we analyzed GC regulation of IL-11 in embryonic bone organ cultures (detection of IL-11 in adult bones was difficult due to the small fraction of osteoblasts in the entire bone). Dex suppressed IL-11 expression in wild type and GR$^{dim}$ bones but not in those from GR$^{Runx2Cre}$ mice (FIG. 7F). Thus, IL-11 expression in the entire bone is similarly regulated by GCs as in isolated osteoblasts.

Suppression of IL-11 in cells and long bones from GR$^{dim}$ mice points towards regulation by a tethering mechanism of the GR, e.g. binding to NF-KB or AP-1. Since Dex efficiently reduced IL-11 mRNA levels in osteoblasts which display strongly impaired NF-KB activity (FIG. 7G), NF-KB is neither involved in IL-11 expression nor a target for suppression by the GR. In contrast, IL-11 expression under osteogenic conditions was strongly impaired in mouse embryonic fibroblasts (MEFs) lacking c-Jun/AP-1 in comparison to wild type MEFs (FIG. 7H). Furthermore, Dex diminished IL-11 mRNA levels in wild type but not in c-Jun knockout MEFs (FIG. 7H), suggesting that c-Jun as a major component of the AP-1 complex drives IL-11 transcription under osteogenic conditions. To corroborate this finding chromatin immunoprecipitation of wild type and $GR^{dim}$ MEFs, in which IL-11 is repressed in a GR dimerization-independent manner (FIG. 12D) was performed. A DNA element of the IL-11 promoter containing two adjacent functional AP-1-binding sites (Tohjima et al., 2003) was amplified from wild type and $GR^{dim}$ MEFs, confirming that the monomeric GR indeed interacts with the AP-1 site on the IL-11 promoter (FIG. 7I). Thus, tethering of the GR monomer to AP-1 forms the basis of GC-mediated inhibition of IL-11.

Figure 13:
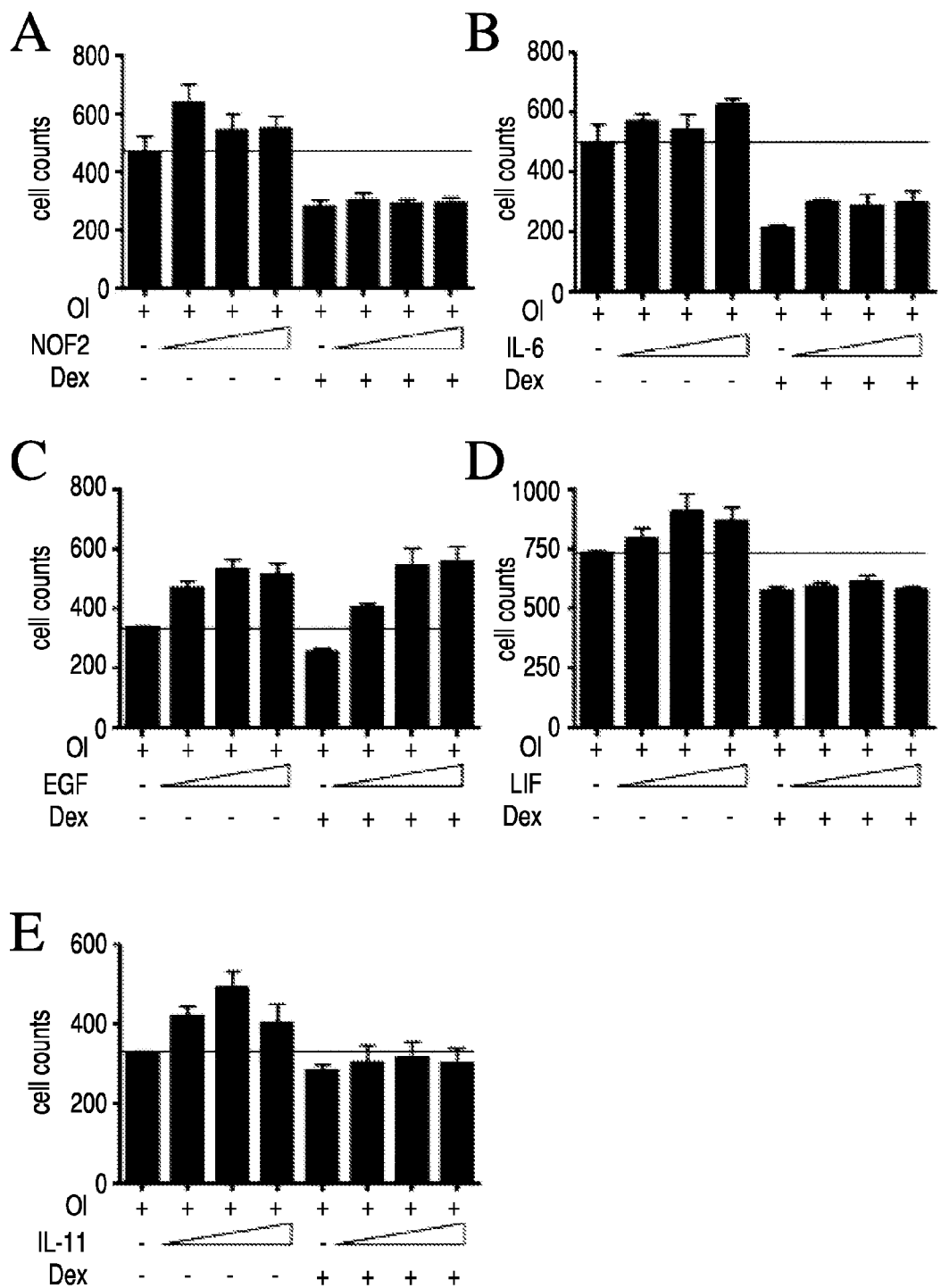
FIG. 13. Effects of GR regulated soluble factors on osteoblast cell numbers. Primary wild type osteoblasts were differentiated with or without Dex and treated with increasing concentrations of NGF2 (A), IL-6 (B), EGF (C) LIF (D) and IL-11 (E). At day 10 cell counts were determined by automatic microscopy. Data are represented as mean+/−SEM. *<0.05.
Figure 14:
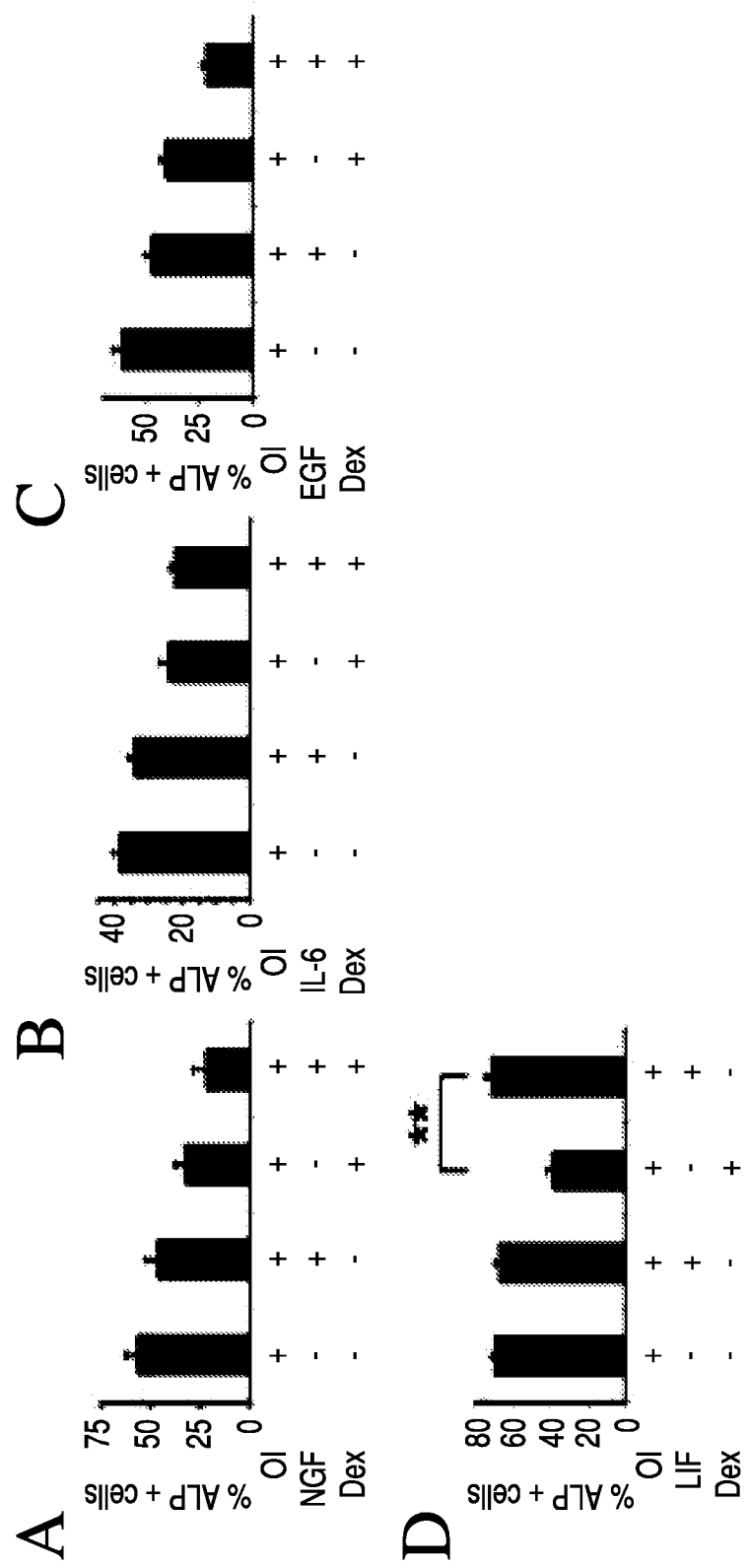
FIG. 14. Effects of GR regulated soluble factors on osteoblast cell differentiation. Primary wild type osteoblasts were differentiated with or without Dex. At day 10 the specific ALP activity was determined and is depicted as ALP positive cells in percent in the absence or presence of NGF (A), IL-6 (B), EGF (C) and LIF (D). Data are represented as mean+/−SEM. * $p<0.05$; ** $p<0.01$.

To investigate whether inhibition of cytokine and growth factor expression underlies the Dex-induced reduction of osteoblast number and differentiation, we ectopically added the previously identified factors to osteoblasts during osteogenic induction in the presence or absence of Dex. NGF2 and IL-6 neither rescued the reduced cell numbers nor the impaired differentiation (FIG. 13A,B, 14A,B). HB-EGF signaling evoked by epidermal growth factor in osteoblasts (Chien et al., 2000) counteracted the reduction in cell number caused by Dex (FIG. 13C), but did not prevent the inhibition of differentiation (FIG. 14C). In contrast, both LIF and IL-11, despite not rescuing the inhibitory effect of Dex on osteoblast cell counts (FIG. 13D,E), potently antagonized the GC-mediated suppression of differentiation (FIG. 14D, 7J,K). In particular, Dex suppression of ALP activity, of Runx2 expression and calcification were fully restored in the presence of IL-11 (FIG. 7K,L). We conclude that LIF and particularly IL-11 are crucial factors in GIO.

Repression of AP-1 Dependent IL-11 Inhibit Osteoblastogenesis

Activation of bona fide GRE-dependent genes, such as GILZ, Per-1 and KLF15 (Balsalobre et al., 2000; Rogatsky et al., 2003; Yoshikawa et al., 2009), was strongly impaired in $GR^{dim}$ osteoblasts, while repression of several genes encoding growth factors and cytokines was not affected. Since inhibition of osteoblastogenesis by GCs was similar in wild type and in $GR^{dim}$ mice, we hypothesized that this was most likely achieved through repression of soluble factors via the monomeric GR. In line with this, we found that HB-EGF, LIF and IL-11 were inhibited by GCs independently of GR dimerization. In agreement to the observation that HB-EGF inhibits differentiation of mesenchymal stem cells (Krampera, 2005), it also exerted an inhibitory effect on osteoblast differentiation. Thus HB-EGF is unlikely to play a role in GIO. In contrary, LIF and IL-11 counteracted suppression of osteoblast differentiation by Dex in culture. Although LIF is a target gene of AP-1 (Bozec et al., 2008) and induces aberrant bone growth in mice (Metcalf and Gearing, 1989), we focused on IL-11 since, in contrast to LIF, it was induced under osteogenic conditions in osteoblasts (data not shown). In entire embryonic bones, suppression of IL-11 by GCs requires the GR in osteoblasts but not its dimerization. This points towards an interaction of the GR monomer with other transcription factors. Our analyses indicate that interaction with NF-KB is not essential for GIO since primary osteoblasts from $dN^{Runx2Cre}$ mice that are impaired in p65 nuclear translocation and thus NF-KB activity responded normally to GCs in terms of diminished cell numbers, induction of apoptosis, inhibition of differentiation and suppression of IL-11. Indeed, inhibition of NF-KB leads to enhanced osteoblast differentiation and bone mass instead of diminished osteoblast function (Chang et al., 2009). However, interaction of the monomeric GR with AP-1 appears to be crucial for inhibition of osteoblast differentiation by GCs. Unlike in wild type cells, IL-11 was hardly induced in cells lacking c-Jun and the residual expression was unaltered by Dex. Consistently, we demonstrated recruitment of the wild type and the $GR^{dim}$ receptor to two adjacent AP-1 sites in the IL-11 promoter (Tohjima et al., 2003). Finally, IL-11 was able to rescue Dex-mediated inhibition of osteoblast differentiation. In line with our results, IL-11 enhances bone formation when overexpressed in mice (Takeuchi et al., 2002) and targeted deletion of the IL-11 receptor alpha leads to decreased bone formation (Sims et al., 2005). Given that the AP-1 target genes IL-11 and LIF are able to rescue Dex-mediated inhibition of osteoblast differentiation, a tethering mechanism involving the monomeric GR and AP-1 presumably underlies repression of cytokines and growth factors during GIO.

Functional Screening Assay for Agents Exhibiting Anti-Inflammatory Activity and that Protect Osteoblast Differentiation 500 Mouse embryonic fibroblasts are seeded per 384 well (2000 cells into a 96 well) until confluency (approx. 2 days). Medium is then replaced and cells are cultured for 5 days with osteogenic inducing medium (alpha-MEM medium, 1% penicillin/streptomycin, 10% fetal calf serum, 100 µg/ml ascorbic acid and 5 mM b-glycerophosphate in the presence or absence of 1 µM dexamethasone (reference compound) or agents or drugs to be tested). After three days, dexamethasone or agents to be tested are withdrawn, and cells are cultured for further three days to differentiate to mature osteoblast like cells. 3.7% Formalin is added (50 µl).

Alternatively, for testing RNAi libraries 20 nM siRNA diluted in OptiMEM® (2.5 µl) is mixed with RNAiMAX®/OptiMEM® (1:25) transfection reagent (2.5 µl) and is plated in one well of a 384 well plate, and incubated for 10 min. Subsequently 1000 mouse embryonic fibroblasts are added (diluted in alpha-MEM medium, 1% penicillin/streptomycin, 10% fetal calf serum) and incubated at 37° C. and 4% CO2 for 48 hours. Medium is subsequently replaced and are cells are cultured for 5 days with osteogenic inducing medium (alpha-MEM medium, 1% penicillin/streptomycin, 10% fetal calf serum, 100 µg/ml ascorbic acid and 5 mM b-glycerophosphate) in the presence or absence of 1 µM dexamethasone. After three days, medium is withdrawn and cells are cultured for further three days to differentiate to mature osteoblast like cells. 3.7% Formalin is added (50 µl).

Differentiation of osteoblasts treated either with agents to be tested or with RNAi will be determined by staining for alkaline phosphatase activity (ALP kit; Sigma, Inc. or ELF® Phosphatase Detection Kit, ATCC). The preserved anti-inflammatory activity is monitored by immunhistochemical staining with antibodies against IL-6 and CXCL10. The avoidance to affect IL-11 and LIF expression is additionally determined by immunohistochemistry as well.

Figure 17:
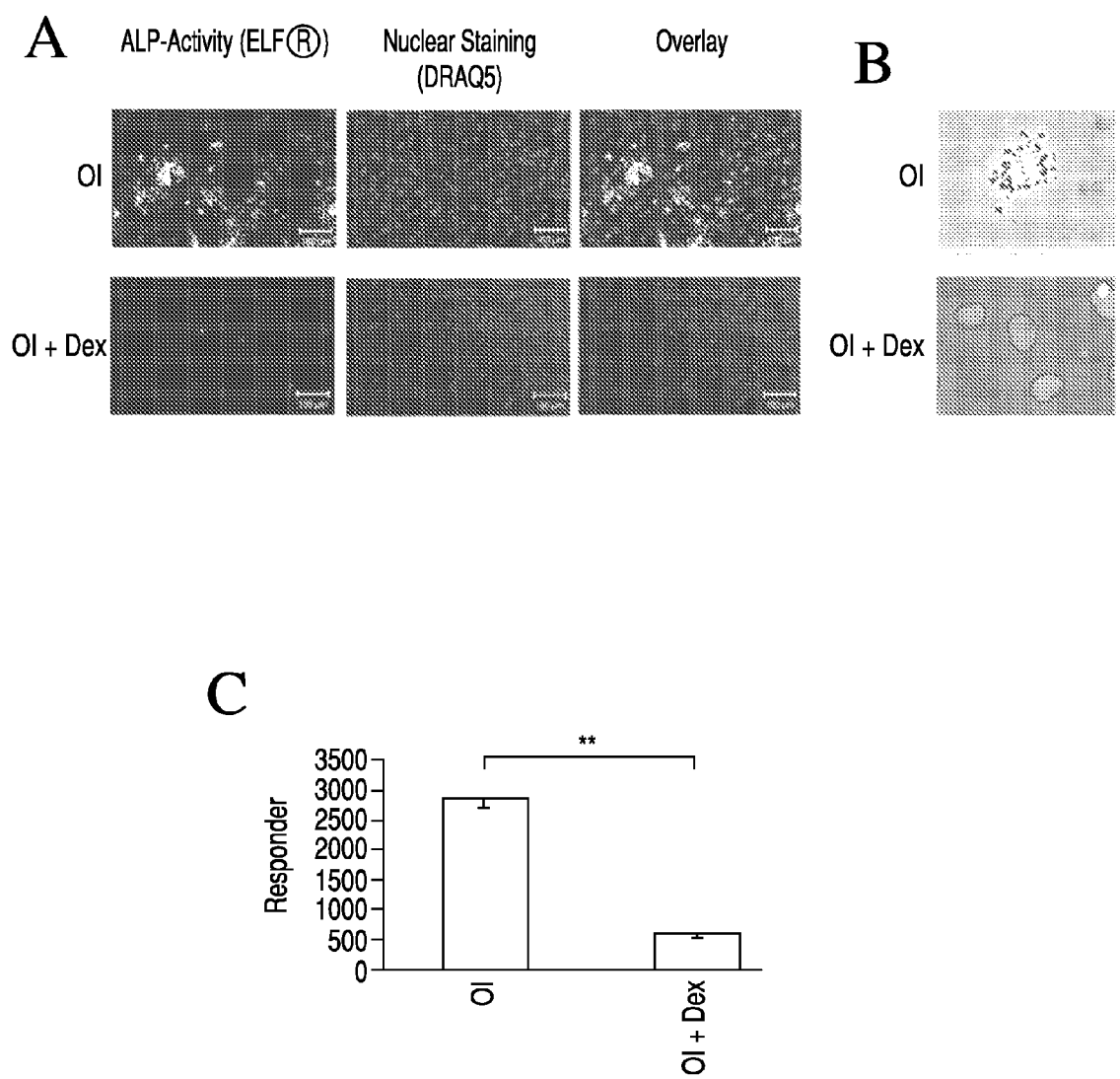
FIG. 17. Automated fluorescent microscopy for high content screening of factors involved in osteoblast differentiation. (A) In osteogenic differentiated (OI) wild type MEFs ALP activity is shown by a fluorescent product (ELF®, green) and nuclei are indicated by DRAQ5® staining (red). Dexamethasone (OI+Dex) is potently reducing ALP activity. (B) Higher magnification reveals cells with spots containing ALP processed substrate (upper panel) which is suppressed in the presence of dexamethasone (lower panel). (C) Summary of cells osteogenic induced (OI) in the absence or presence of dexamethasone (OI+Dex) containing at least 5 spots of fluorescent ALP activity analyzed automatically by automatic microscopy using ArrayScan V™.
Figure 18:
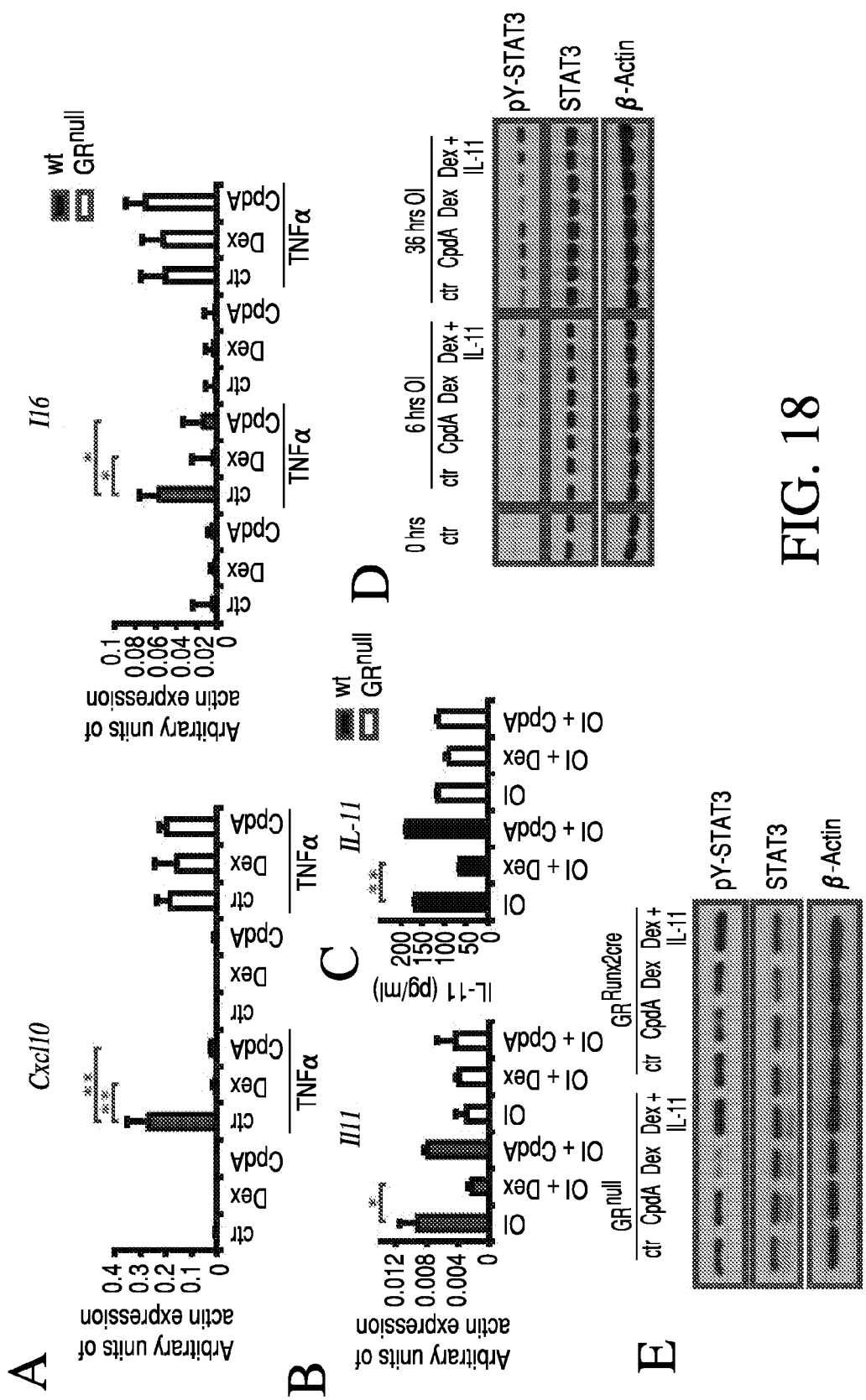
FIG. 18. CpdA inhibits proinflammatory gene expression but not IL-11 signaling in primary osteoblasts. A) Primary osteoblasts of wild-type (wt) or $GR^{null}$ mice were treated either in the presence of or without TNF-alpha in combination with $10^{-6}$ M Dex, $10^{-6}$ M CpdA, or solvent (ctr) for 6 h. mRNA expression levels of chemokine Cxcl10 and IL-6 were analyzed, the measurement was carried out as arbitrary units of actin expression. Osteogenic-induced (OI) primary osteoblasts of wt and $GR^{null}$ mice were cotreated with $10^{-6}$ M Dex or $10^{-6}$ M CpdA. B) After 6 h of cultivation, IL-11 mRNA expression levels were measured from total RNA extracts. C) IL-11 protein was measured in the supernatant using ELISA after 36 h of culture (n=3; Beta-actin was used for standardisation). *P<0.05, **P<0.01; 1-way ANOVA followed by Dunnett's multiple comparison test. D) Western blot analysis is shown of phosphorylated STAT3 levels in primary osteoblasts treated for 6 or 36 h with $10^{-6}$ M Dex, $10^{-6}$ M Dex plus 5 ng/ml IL-11, or $10^{-6}$ M CpdA under OI conditions. E) Western blot analysis is shown for STAT3 phosphorylation of bones from $GR^{Runx2Cre}$ mice subjected to organ cultures, treated as in D for 36 h.
Figure 19:
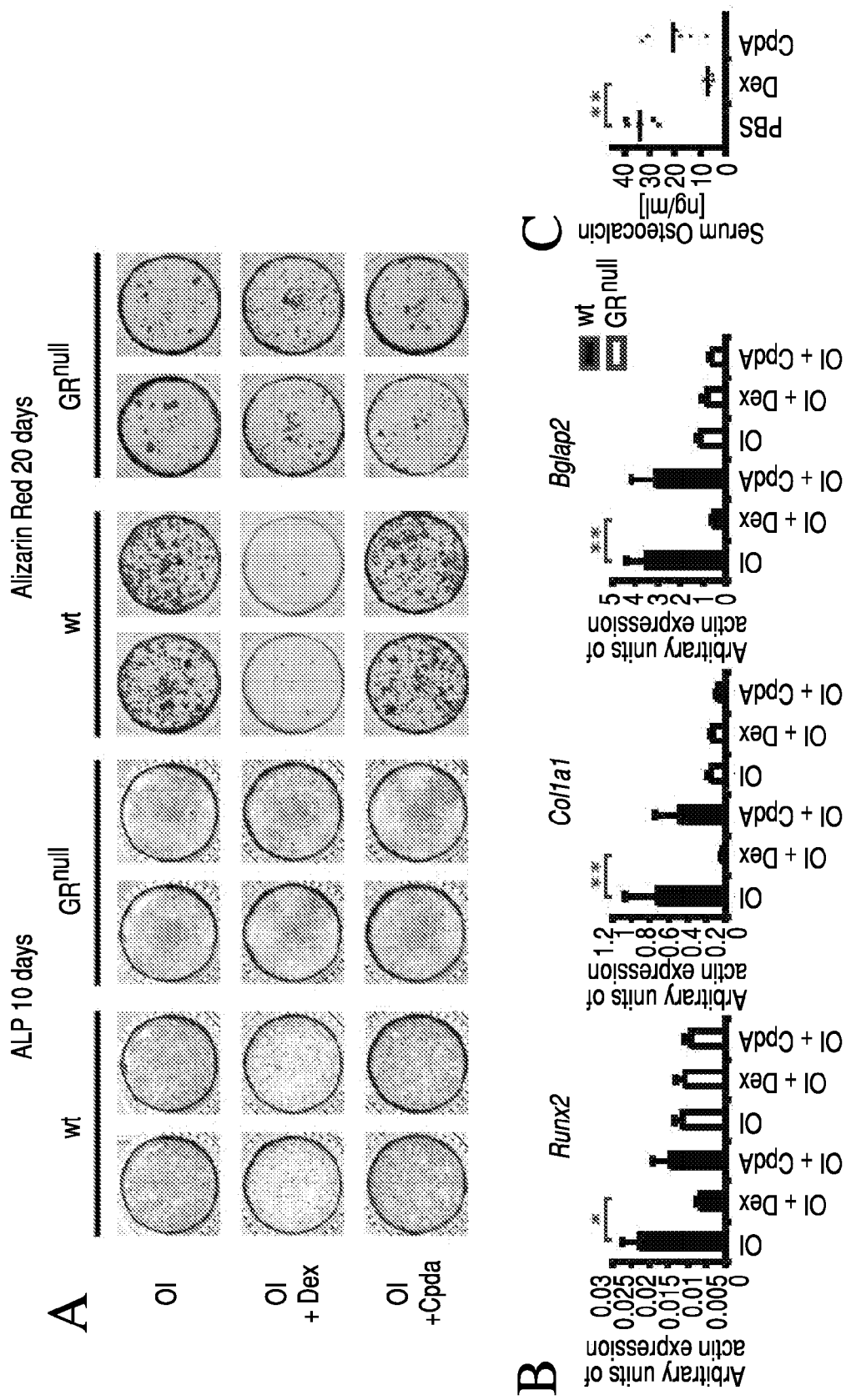
FIG. 19. CpdA does not affect osteoblast differentiation and osteoblast markers in vitro and in vivo. Primary osteoblasts of wild-type (wt) and $GR^{null}$ mice were subjected to OI differentiation during treatment with $10^{-6}$ M Dex or $10^{-6}$ M CpdA. A) Cells were fixed and stained for ALP activity after 10 d and for mineralization of the matrix using Alizarin red after 20 d of culture. B) mRNA expression levels of osteoblast marker genes are shown, indicated as arbitrary units of actin expression. Col1a1 and Runx2 at d 10 and Bglap2/osteocalcin at d 20 of differentiation (n=3; Beta-actin was used for normalization). *P<0.05, **P<0.01; 1-way ANOVA followed by Dunnett's multiple comparison test. C) DBA/1 mice were treated daily with Dex (62.5 ug), CpdA (300 ug), or solvent (PBS) for 8 d. Serum was collected according to standard procedures, and ELISA was performed for the measurement of osteocalcin levels (n=5 for PBS; n=6 for CpdA; n=7 for Dex). *P<0.05, **P<0.01; Kruskal-Wallis test followed by Dunn's multiple comparison test.
Figure 20:
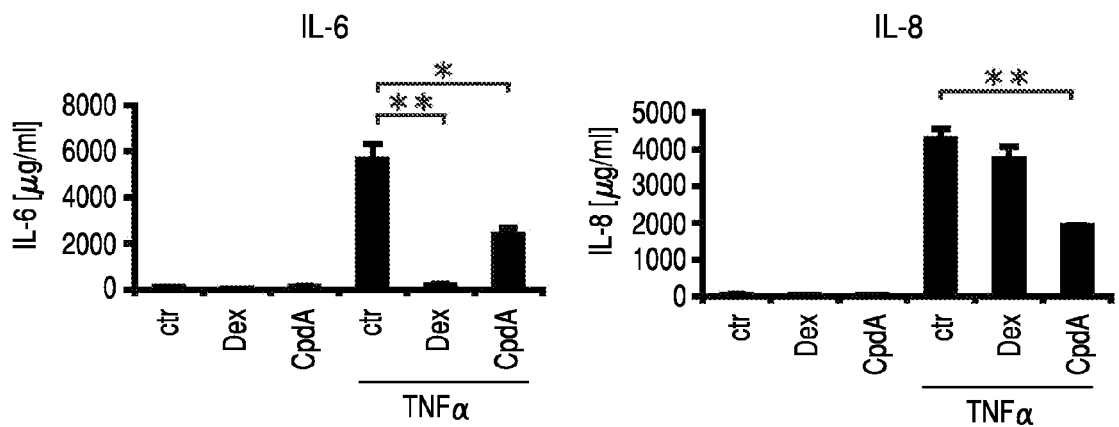
FIG. 20. ELISA determination of protein levels of Interleukins 6 (IL-6) and 8 (IL-8) in terminally differentiated human fetal osteoblasts (hFOB). Terminally differentiated human fetal osteoblasts (hFOB) were treated as FLS cells.

After fixation, the wells are stained with the nuclear stain DRAQ5 and a fluorescent substrate (ELF) for alkaline phosphatase activity. This allows monitoring cellular ALP activity by automatic microscopy and evaluation with the respective software (FIG. 17).

Immunohistochemical staining towards the antibodies IL-6, CXCL10, IL-11 and/or LIF follows as a last step. Fluorescent signals of the antibodies will be monitored by automatic microscopy and evaluation with the respective software. Dexamethasone treatment strongly reduces ALP positive cells, a readout for impairment of differentiation and suppress all cytokines. Molecular compounds (agents) that suppress NF-KB dependent IL-6 and/or CXCL10 expression but do not affect the AP-1 dependent IL-11 and/or LIF expression, nor affect differentiation (i.e. number of ALP positive cells), are considered putative anti-inflammatory acting hits with reduced side effects on bone formation. Any number of drugs, small compounds, or other agents can be tested using the method as described herein.

Compound a Exhibits Anti-Inflammatory Activity but does not Inhibit Osteoblast Differentiation.

We demonstrate that the capacity of the monomeric GR to inhibit AP-1-controlled cytokines, such as IL-11 or LIF, is central to the suppression of osteoblast differentiation and that inhibition of bone formation by GCs is independent of GR dimerization. Consequently, tethering of the GR to AP-1 not only contributes to the anti-inflammatory effects of GCs but is also essential for provoking GIO. In contrast, repression of NF-KB-dependent genes does not seem to be involved in osteoblast differentiation, whereas it plays a major role in the anti-inflammatory activities of GCs.

This suggests that selective GR agonists, which would fail to suppress AP-1-dependent gene expression but are still capable of inhibiting NF-KB-dependent gene regulation, are beneficial in anti-inflammatory activities while not concomitantly inducing GIO.

Compound A was tested for its anti-inflammatory activity in addition to its effect on osteoblast differentiation (FIGS. 18-22). The experiments carried out demonstrate that CpdA inhibits proinflammatory gene expression but not IL-11 signaling in primary osteoblasts. Additionally, it is shown that CpdA does not affect osteoblast differentiation and osteoblast markers in vitro and in vivo. When tested using the method of the present invention CpdA tested as a hit, further demonstrating that CpdA exhibits the inventive properties of the present invention.

Compound A, derivatives thereof and/or other agents identified using the methods of the present invention have been applied in animal studies, which demonstrate promising results. The effects and properties of the methods and agents disclosed herein, regarding both in vitro and in vivo experiments, are transferable to other animal models and to human subjects in the case of therapeutic approaches.

LIF Prevents GC Induced Bone Loss

In the experiments described above, it is shown that GC induced osteoporosis (GIO) depends on GR monomer interference with AP-1 regulated target genes. One of AP-1 regulated target genes in bone is encoded by the Leukemia inhibitory factor (LIF) gene (Bozec, A. et al). We found this gene down regulated by the GR monomer. Furthermore the addition of LIF recombinant protein added to tissue cultures ameliorated the inhibition of osteoblast differentiation by GCs.

In order to further demonstrate that the administration of LIF can counteract GC induced bone loss we treated 9 week old female FVB/N mice with or without prednisolone and in the presence or absence of LIF administration. After 15 days the bone mineral density was determined by micro computertomography (FIG. 23). LIF administration increases bone mass (bone volume/tissue volume (Fig. A, B) in "sham (i.e. control)" treated animals and prednisolone treated animals. Despite a prednisolone mediated reduction of trabecular thickness that also occurs in LIF treated animals (Fig. C), a strong increase of trabecular number occurs upon LIF treatment (Fig. D) which is pivotal to enhance bone mass (Fig. A, B).

Experimental Procedures Used in the Examples

Generation of Runx2Cre Mice:

See supplementary information A 150-kb BAC covering the Runx2 locus (Genome System BAC Library, RZPD, Germany) was modified by inserting a codon-improved Cre recombinase at the translational start site of the bone-specific distal promoter (P1) of the Runx2 gene (Stock and Otto, 2005) by ET-recombination as previously described (Casanova et al., 2001). The modified BAC was microinjected into the pronucleus of oocytes from FVB/N mice and three different founder lines were established. One line was chosen for crossing with $GR^{flox}$ mice based on its expression pattern.

Animal Experimentation:

All animal experiments were performed in accordance with accepted standards of animal welfare and with permission of the responsible authorities of Baden-Württemberg and Thüringen. $GR^{null}$ (Tronche et al., 1998), $GR^{dim}$ (Reichardt et al., 1998), $GR^{flox}$ (Tronche et al., 1998) and $dN^{flox}$ (Schmidt-Ullrich et al., 2001) mice were backcrossed to the FVB/N background for at least four generations. Cre activity was monitored using Rosa26 reporter mice by whole-mount b-galactosidase staining (Soriano, 1999). $GR^{LysMCre}$ mice (Tuckermann et al., 2007) were backcrossed to Balb/c for five generations. To induce osteoporosis, prednisolone (or a placebo control) was applied for 14 days by subcutaneous implantation of slow-release pellets resulting in a calculated dose of 12.5 mg/kg/d (15 mg; 60-day release; Innovative Research of America, Inc.) in 10-week-old female mice.

Cell Culture and qRT-PCR Analysis:

Primary osteoblasts were isolated from either embryonic (E18.5) or neonatal calvaria by sequential digestions and cultivated as previously described (David et al., 2005). c-Jun-deficient cells were obtained from previously described mice (Schreiber et al., 1999). Cells were passaged once before induction of osteogenic differentiation by 100 µg/ml ascorbic acid and 5 mM b-glycerophosphate in the presence or absence of 1 µM Dex (Sigma). Differentiation of osteoblasts was determined by staining for ALP activity (ALP kit, Sigma or ELF® Phosphatase Detection Kit, ATCC) or by Alizarin Red staining (Sigma) at indicated time points. Apoptosis was detected by In situ Cell Death Detection Kit (Roche), and proliferation with fluorescent immunohistochemistry using mouse anti-Ki-67 (BD Pharmingen™) and Alexa Fluor® 594-labeled donkey anti-mouse IgG (Molecular Probes™). Quantification of the stainings and cell numbers according to DAPI labeling was performed by automated microscopy using Cellomics ArrayScan and software HCS Scan® (Thermo-Fischer). The factors EGF (Calbiochem), NGF2 (Sigma), IL-6 (ImmunoTools), IL-11 (Antigenix America, Inc.) and LIF (Chemicon) were added to the culture after differentiation at concentrations of 0.8, 4 and 20 ng/ml. qRT-PCR was performed as previously described (Tuckermann et al., 2007). Primer information can be provided upon request. Statistical differences between the groups of cultures (n=3-6) were assessed by the Student's t-test.

CFU-OBs:

CFU-OBs per leg were obtained by counting Alizarin Red-positive colonies of $2\times10^6$ bone marrow cells (excluding erythrocytes) plated per 6-well after 20 days under osteogenic conditions.

Co-Culture Experiments:

Co-cultures were established as previously described (David et al., 2005). Briefly, $0.5\times10^6$ fetal liver cells isolated from wild type or $GR^{null}$ embryos were placed on top of wild type, $GR^{dim}$ or $GR^{null}$ osteoblasts in the presence of 10 nM colecalciferol with or without 1 µM Dex per 24-well. Primary osteoclasts were derived from bone marrow of wild type and $GR^{dim}$ mice in the presence of 50 ng/ml recombinant murine M-CSF and 30 ng/ml recombinant murine RANKL (R&D Systems). TRAP-positive cells were stained after seven days with the leukocyte acid phosphatase kit (Sigma) and counted per 24-well. Osteoclast apoptosis was measured with ELISA (Cell death detection ELISA, Roche). Resorption was assessed by seeding bone marrow cells on osteocyte chambers in the presence of RANKL and M-CSF, with or without Dex, and determination of resorption pits by von Kossa staining followed by microscopy.

Immunoblotting:

Primary dN$^{Runx2Cre}$ osteoblasts were treated with TNF-alpha (Sigma) for 30 min. Immunoblotting was performed with the nuclear (25 μg) and cytoplasmic (40 μg) protein fractions using rabbit anti-RelA, rabbit anti-PolII and goat anti-b-actin (Santa Cruz).

Radiographic Analysis and Alizarin Red/Alcian Blue Staining:

Whole skeletons were analyzed by contact radiography using a Faxitron X-ray cabinet (Faxitron X-ray Corp., Wheeling, Ill., USA). For differential staining of bone, E17.5 embryos were prepared according to the method of C. Arnott (Kaufmann, 2003).

Histomorphometry:

Parameters of static and dynamic histomorphometry were quantified on toluidine blue-stained undecalcified proximal tibia and lumbar vertebral sections as described previously (Amling et al., 1999) using the Osteo-histomorphometry system (Osteometrics, Atlanta, Ga., USA) (Parfitt et al., 1987). Osteocytes were assessed at the cortical bone by OsteoMeasure™ software. To assess dynamic histomorphometric indices, mice were given two injections of calcein, nine and two days before dissection. Fluorochrome measurements for the determination of the bone formation rate were performed on two nonconsecutive 12-μm-thick sections for each animal. Statistical differences between the groups (n=5-6) were assessed by the Student's t-test.

Osteoblast Proliferation and Apoptosis In Vivo:

Mice were treated with prednisolone (12.5 mg/kg/d) for one day and they got pulsed with 10 μg/g body weight BrdU 4 hours before dissection. Decalcified deparaffined femur sections were stained with the In situ Cell Death Detection Kit (Roche) for apoptosis and rat anti-BrdU (Abcam) following Peroxidase coupled anti-rat IgG for proliferation.

LIF Administration:

Female 9 week old FVB/N mice were treated with control pellets (sham), prednisolone (Pred) releasing pellets (12 mg/kg/day releasing rate) and were treated one day later with PBS and LIF i.p. injections twice a day (0.2 mg/kg/day) until 15 days. Mice were sacrificed on day 16.

Once given the above disclosure, many other features, modifications, and improvements will become apparent to the skilled artisan. Such other features, modifications, and improvements are therefore considered to be part of this invention, the scope of which is to be determined by summary of the invention and the following claims.

REFERENCES

Balsalobre, A., et al. (2000) Science 289, 2344-2347.
Bozec, A., et al. (2008) Nature 454, 221-225.
Canalis, E., et al. (2007) Osteoporos Int 18, 1319-1328.
Casanova, E., et al. (2001) Genesis 31, 37-42.
Chang, J., et al. (2009) Nat Med 15, 682-689.
Chien, H. H., et al. (2000) Calcified tissue international 67, 141-150.
David, J. P., et al. (2005) J Clin Invest 115, 664-672.
Durbridge, et al. (1990) Calcified tissue international 47, 383-387.
Hofbauer, et al. (1999) Endocrinology 140, 4382-4389.
Hofbauer, L. C., et al. (2009) Arthritis Rheum 60, 1427-1437.
Ishida, Y., and Heersche, J. N. (1998) J Bone Miner Res 13, 1822-1826.
James, C. G., et al. (2007) BMC genomics 8, 205.
Jia, D., et al. (2006) Endocrinology 147, 5592-5599.
Kalak, R., et al. (2009) Bone, 1-35.
Kassel, O., and Herrlich, P. (2007) Mol Cell Endocrinol 275, 13-29.
Kim, H. J., et al. (2006) J Clin Invest 116, 2152-2160.
Krampera, M. (2005) Blood 106, 59-66.
Metcalf, D., and Gearing, D. P. (1989) Proc Natl Acad Sci USA 86, 5948-5952.
Reichardt, H. M., et al. (1998) Cell 93, 531-541.
Reichardt, H. M., et al. (2001) Embo J 20, 7168-7173.
Rogatsky, I., et al. (2003) Proc Natl Acad Sci USA 100, 13845-13850.
Schmidt-Ullrich, R., et al. (2001) Development 128, 3843-3853.
Schreiber, M., et al. (1999) Genes Dev 13, 607-619.
Shalhoub, V., et al. (1992) J Cell Biochem 50, 425-440.
Sher, L. B., et al. (2006) Calcified tissue international 79, 118-125.
Sher, L. B., et al. (2004) Endocrinology 145, 922-929.
Sims, N. A., et al. (2005) J Bone Miner Res 20, 1093-1102.
Smith, E., et al. (2000) J Biol Chem 275, 19992-20001.
Soriano, P. (1999) Nat Genet. 21, 70-71.
Stock, M., and Otto, F. (2005) J Cell Biochem 95, 506-517.
Takeuchi, Y., et al. (2002) J Biol Chem 277, 49011-49018.
Tohjima, E., et al. (2003) J Bone Miner Res 18, 1461-1470.
Tronche, F., et al. (1999) Nat Genet. 23, 99-103.
Tronche, F., et al. (1998) Curr Opin Genet Dev 8, 532-538.
Tuckermann, J. P., et al. (2007) J Clin Invest 117, 1381-1390.
Weinstein, R. S., et al. (2002) J Clin Invest 109, 1041-1048.
Weinstein, R. S., et al. (1998) J Clin Invest 102, 274-282.
Yao, W., et al. (2008) Arthritis Rheum 58, 1674-1686.
Yoshikawa, N., et al. (2009) AJP: Endocrinology and Metabolism 296, E1363-E1373.
Amling, M., et al. (1999) Endocrinology 140, 4982-4987.
Kaufmann, M. H. (2003). The Atlas of Mouse development, 6th edn (San Diego, Elsevier Academic Press).
Parfitt, A. M., et al. (1987) J Bone Miner Res 2, 595-610.
van Loo et al., Molecular Endocrinology, (2010), 24(2), 310-322
Gossye et al., Annals of the Rheumatic Diseases, (2010), 69(1), 291-296
Wuest et al., PLoS One, (2009), 4 (12)
Gossye et al., Arthritis & Rheumatism, (2009), 60(11), 3241-3250
Zhang et al., Journal of Immunology, (2009), 183(5), 3081-3091
Haegeman et al., Pharmacologyonline, (2006), (3), 545-548
De Bosscher et al., PNAS, (2005), 102(44), 15827-15832
Kurahashi et al., Endocrine, (2005), 102(44), 15827-15832

What we claim is:

1. A method for counteracting glucocorticoid (GC)-induced bone loss comprising
    administering to a subject undergoing GC treatment leukemia inhibitory factor (LIF) protein in an amount effective for counteracting the GC-induced bone loss in the subject.

2. The method according to claim 1, wherein said subject suffers from a medical condition associated with inflammation and wherein nuclear factor kappa-light-chain-enhancer of activated B-cells (NF-KB) activity is inhibited in said subject.

3. The method according to claim 2, wherein the medical condition is an allergy, autoimmune disease, arthritis or cancer.

4. The method according to claim 2, wherein GC is administered to said subject in an amount effective to inhibit NF-KB activity.

5. The method according to claim 4, wherein the GC is prednisolone.

6. The method according to claim 4, wherein the GC is prednisone.

7. The method according to claim 1, wherein the LIF is recombinant human LIF.

8. The method according to claim 1, wherein the LIF and GC are administered to said subject simultaneously or in combination.

9. The method according to claim 1, wherein glucocorticoid-mediated suppression of osteoclast differentiation is reduced or alleviated.

10. The method according to claim 1, wherein the LIF is administered in the form of a pharmaceutical composition comprising a pharmaceutically acceptable carrier.

11. The method according to claim 10, wherein the pharmaceutically acceptable carrier is poly(lactic-co-glycolic) acid (PLGA).

12. The method according to claim 11, wherein the LIF-containing pharmaceutical composition comprises PLGA-based nanoparticles.

13. A method for increasing a trabecular number in a subject undergoing GC treatment comprising
administering LIF protein to said subject undergoing GC treatment in an amount effective to counteract GC-induced reduction of bone volume in the subject.

14. The method according to claim 13, wherein said subject suffers from a medical condition associated with inflammation and wherein NF-KB activity is inhibited in said subject.

15. The method according to claim 14, wherein the medical condition is an allergy, autoimmune disease, arthritis or cancer.

16. The method according to claim 14, wherein GC is administered to said subject in an amount effective to inhibit NF-KB activity.

17. The method according to claim 16, wherein the GC is prednisolone.

18. The method according to claim 16, wherein the GC is prednisone.

19. A method for ameliorating glucocorticoid (GC)-induced inhibition of osteoblast differentiation comprising
administering to a subject undergoing GC treatment leukemia inhibitory factor (LIF) protein in an amount effective for ameliorating the GC-induced inhibition of osteoblast differentiation in the subject.

* * * * *